US011723894B2

(12) United States Patent
Perez Castillo et al.

(10) Patent No.: US 11,723,894 B2
(45) Date of Patent: Aug. 15, 2023

(54) COMBINATION PRODUCT FOR THE TREATMENT OF NEUROLOGICAL AND/OR PSYCHIATRIC DISORDERS

(71) Applicants: Consejo Superior de Investigaciones Cientificas (CSIC), Madrid (ES); Universidad Autónoma de Madrid, Madrid (ES); CENTRO DE INVESTIGATIÓN BIOMÉDICA EN RED DE ENFERMEDADES NEURODEGENERATIVAS, Madrid (ES); BlumenTech, S.L., Barcelona (ES); Institut de Recerca de l'Hospital de la Santa Creu i Sant Pau, Barcelona (ES)

(72) Inventors: Ana Maria Perez Castillo, Madrid (ES); Jordi Riba Serrano, Barcelona (ES); Jose Ángel Morales García, Madrid (ES)

(73) Assignee: TERRAN BIOSCIENCES, INC., New York, NY (US)

( * ) Notice: Subject to any disclaimer, the term of this patent is extended or adjusted under 35 U.S.C. 154(b) by 23 days.

(21) Appl. No.: 16/958,226

(22) PCT Filed: Oct. 26, 2018

(86) PCT No.: PCT/EP2018/079503
§ 371 (c)(1),
(2) Date: Jun. 26, 2020

(87) PCT Pub. No.: WO2019/081764
PCT Pub. Date: May 2, 2019

(65) Prior Publication Data
US 2020/0397752 A1 Dec. 24, 2020

(30) Foreign Application Priority Data
Oct. 26, 2017 (EP) .................................. 17382718

(51) Int. Cl.
| A61P 25/00 | (2006.01) |
| A61K 45/06 | (2006.01) |
| A61K 31/4045 | (2006.01) |
| A61P 25/16 | (2006.01) |
| A61K 31/498 | (2006.01) |
| A61K 31/519 | (2006.01) |

(52) U.S. Cl.
CPC ........ *A61K 31/4045* (2013.01); *A61K 31/498* (2013.01); *A61K 31/519* (2013.01); *A61P 25/16* (2018.01)

(58) Field of Classification Search
None
See application file for complete search history.

(56) References Cited

U.S. PATENT DOCUMENTS

| 3,075,992 A | 1/1963 | Hofmann et al. |
| 2012/0289515 A1 | 11/2012 | Migaly |
| 2014/0350064 A1* | 11/2014 | Chen .................. A61K 31/4045 |
| | | 514/415 |
| 2015/0231126 A1 | 8/2015 | Peters et al. |
| 2017/0281652 A1 | 10/2017 | Altschul et al. |
| 2019/0350949 A1 | 11/2019 | Kucuksen et al. |
| 2020/0179349 A1 | 6/2020 | Yun et al. |
| 2022/0273680 A1 | 9/2022 | Scott |

FOREIGN PATENT DOCUMENTS

| WO | WO-2018135943 A1 | 7/2018 |
| WO | WO-2019081764 A1 | 5/2019 |
| WO | WO-2021030571 A1 | 2/2021 |

OTHER PUBLICATIONS

Kometer et al., Biol. Psyciatry, 2012, 72(11), pp. 898-906. (Year: 2012).*
Marta Valle, et al, "Inhibition of alpha oscillations through serotonin-2A receptor activation underlies the visual affects of ayahuasca in humans", European Neuropsychopharmacology, 2016, pp. 1161-1175, 26.
Michael Kometer, et al, "Psilocybin Biases Facial Recognition, Goal-Directed Behavior, and Mood State Toward Positive Relative to Negative Emotions Through Different Serotonergic Subreceptors", Biological Psychiatry, 2012, pp. 898-906, 72.
Filip Tyls, et al, "Sex differences and serotonergic mechanisms in the behavioural effects of psilocin", Behavioural Pharmacology, 2016, pp. 309-320, vol. 27, No. 4.
Briony J. Catlow, et al, "Effects of psilocybin on hippocampal neurogenesis and extinction of trace fear conditioning", Experimental Brain Research, 2013, pp. 481-491, 228.
Fred H. Gage, Mammalian Neural Stem Cells, Science, 2000, pp. 1433-1438, vol. 287, No. 5457.
Sally Temple, Stem cell plasticity—building the brain of our dreams, Nature Reviews Neuroscience, Jul. 2001, pp. 513-520, vol. 2.
Clara Herrera-Arozamena, et al, Recent Advances in Neurogenic Small Molecules as Innovative Treatments for Neurodegenerative Diseases, Molecules, 2016, pp. 1-21, 1165.
Shih-Jen Chen, et al, Antidepressant Administration Modulates Neural Stem Cell Survival and Serotoninergic Differentiation Through Bel-2, Current Neurovascular Research, 2007, pp. 19-29, 4.
Maura Boldrini et al, Antidepressants increase neural progenitor cells in the human hippocampus, Neuropsychopharmacology, Oct. 2009, pp. 2376-2389, 34 (11).

(Continued)

*Primary Examiner* — Brian Gulledge
(74) *Attorney, Agent, or Firm* — Wilson Sonsini Goodrich & Rosati

(57) ABSTRACT

The present application provides a combination product for the treatment and/or prevention of psychiatric and/or neurological disorders. The combination product comprises (i) a compound which promotes neurogenesis and has hallucinogenic and/or psychedelic side effects, and (ii) a 5-HT2A receptor antagonist which alleviates and/or removes the hallucinogenic and/or psychedelic side effects caused by the first compound.

10 Claims, 8 Drawing Sheets

(56) References Cited

OTHER PUBLICATIONS

Figure 1:
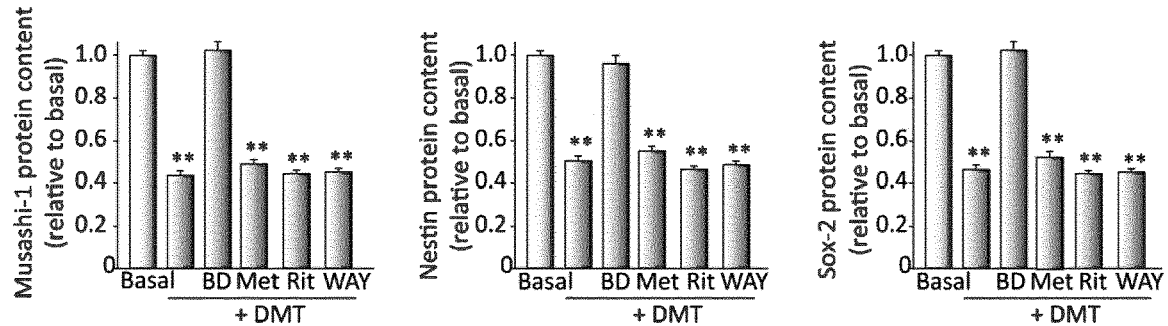

Benjamin D. Sachs, et al, Chronic Fluoxetine Increases Extra-Hippocampal Neurogenesis in Adult Mice, International Journal of Neuropsychopharmacology, 2015, pp. 1-12.
Jordi Riba, et al, Human Pharmacology of Ayahuasca: Subjective and Cardiovascular Effects, Monoamine Metabolite Excretion, and Pharmacokinetics, The Journal of Pharmacology and Experimental Therapeutics, 2003, pp. 73-83, vol. 306, No. 1.
Rick J. Strassman, MD., et al, Dose-Response Study of N, N-Dimethyltryptamine in Humans, Archives of General Psychiatry, Feb. 1994, pp. 98-108, vol. 51.
D.J. McKenna, et al, Differential Interactions of Indolealkylamines with 5-Hydroxytryptamine Receptor Subtypes, Neuropharmacology, 1990, pp. 193-198, vol. 29 No 3.
Anna Rickli, et al, Receptor interaction profiles of novel psychoactive tryptamines compared with classic hallucinogens, European Neuropharmacology, 2016, pp. 1-11.
Dominique Fontanilla et al, The Hallucinogen N, N-Dimethyltryptamine (DMT) Is an Endogenous Sigma-1 Receptor Regulator, Science, 2009, pp. 934-937, 323 (5916).
David E. Nichols, Hallucinogens, Pharmacology & Therapeutics 101, 2004, pp. 131-181.
Teruo Hayashi, et al, Sigma-1 Receptor Chaperones at the ER-Mitochondrion Interface Regulate Ca2+ Signaling and Cell Survival, Cell, 2007, pp. 596-610, 131.
Tomohisa Mori et al, Sigma-1 Receptor Chaperone at the ER-Mitochondrion Interface Mediates the Mitochondrion-ER-Nucleus Signaling for Cellular Survival, Plos One, 2013, pp. 1-13, vol. 8 Issue 10.
Arin Dam Pal, et al, The sigma-1 receptor protects against cellular oxidative stress and activates antioxidant response elements, European Journal of Pharmacology, 2012, pp. 12-20, 682 (1-3).
T Omi, et al, Fluvoxamine alleviates ER stress via induction of Sigma-1 receptor, Cell Death and Disease, 2014, 5, e1332.
Atilla Szabo et al, Psychedelic N,N-Dimethyltryptamine and 5-Methoxy-N,N-Dimetheyltryptamine Modulate Innate and Adaptive Inflammatory Responses through the Sigma-1 Receptor of Human Monocyte-Derived Dendritic Cells, Plos One, 2014, pp. 1-12, vol. 9 Issue 8 e106533.
Karsten Ruscher, et al., The involvement of the sigma-1 receptor in neurodegeneration and neurorestoration, Journal of Pharmacological Sciences, 2015, pp. 30-35, 127.
Atilla Szabo, et al, Dimethyltryptamine (DMT): a biochemical Swiss Army knife in neuroinflammation and neuroprotection?, Neural Regeneration Research, 2016, pp. 396-397, vol. 11 Issue 3.
Ede Frecska, et al, The Therapeutic Potentials of Ayahuasca: Possible Effects again Various Diseases of Civilization, Frontiers in Pharmacology, 2016, pp. 1-17, vol. 7 Article 35.
Atilla Szabo, et al, The Endogenous Hallucinogen and Trace Amine N,N-Dimethyltryptamine (DMT) Displays Potent Protective Effects against Hypoxia via Sigma-1 Receptor Activation in Human Primary iPSC-Derived Cortical Neurons and Microglia-Like Immune Cells, Frontiers in Neuroscience, 2016, pp. 1-11, vol. 10 Article 423.
Flavia De L Osorio et al, Antidepressant effects of a single dose of ayahuasca in patients with recurrent depression: a preliminary report, Revista Brasileira de Psiquiatria, 2015 pp. 13-20, 37.
Roberta Tittarelli et al., Recreational Use, Analysis and Toxicity of Tryptamines, Current Neuropharmacology, 2015 pp. 26-46, 13.
Thomas S. Ray, Psychedelics and the Human Receptorome, Plos One, 2010, pp. 1-17, vol. 5, Issue 2 e9019.
Franz X. Vollenweider, et al, Psilocybin induces schizophrenia-like psychosis in humans via a serotonin-2 agonist action, Neuroreport, 1998, pp. 3897-3902, vol. 9 No 17.
Katrin H. Preller, et al., The Fabric of Meaning and Subjective Effects in LSD Induced States Depend on Serotonin 2A Receptor Activation, Current Biology, 2017, pp. 451-457, 27.
Ya-Zhu Xu, et al, Synthesis of deuterium labeled standards of 5-methoxy-N,N-dimethyltryptamine (5-Meo-DMT), Journal of Labelled Compounds and Radiopharmaceuticals, 2006, pp. 897-902, 49.

Hofmann et al., 168. Psilocybin und Psilocin, Helvetica Chimica Acta, 1959, pp. 1557-1572, vol. 42 No. 5.
Nicholas V. Cozzi, et al, Receptor binding profiles and quantitative structure-affinity relationships of some 5-substituted-N,N-diallyltryptamines, Bioorganic & Medicinal Chemistry Letters, 2016, pp. 959-964, vol. 26 No. 3.
Adam L. Halberstadt et al., Behavioral effects of $\alpha,\alpha,\beta,\beta$-tetradeutero-5-MeO-DMT in rats: comparison with 5-MeO-DMT administered in combination with a monoamine oxidase inhibitor, Psychopharmacology, 2012, pp. 709-718, vol. 221 No. 4.
John M. Beaton et al., A Comparison of the Behavioral Effects of Proteo- and Deutero-N, N-Dimethyltryptamine, Pharmacology Biochemistry & Behavior, 1982, pp. 811-814, vol. 16 No. 5.
Jose A. Morales-Garcia et al., Phosphodiesterase7 Inhibition Activates Adult Neurogenesis in Hippocampus and Subventricular Zone in Vitro and in Vivo, Stem Cells, 2017, pp. 458-472, vol. 35.
Michael T. Heneka, et al., Neuroinflammation in Alzheimer's Disease, Lancet Neurol., 2015, pp. 388-405, vol. 14 No. 4.
Simon D. Brandt, et al, Characterization of the synthesis of N,N-dimethyltryptamine by reductive amination using gas chromatography ion trap mass spectrometry, Drug Testing and Analysis, 2010, pp. 330-338, 2.
Masanori Somei, et al, The Chemistry of Indoles. CVII.1) A Novel Synthesis of 3,4,5,6-Tetrahydro-7-hydroxy-1H-azepino[5,4,3-cd]indoles and a New Finding on Pictet-Spengler Reaction, Chemical and Pharmaceutical Bulletin (Tokyo), 2001, pp. 1159-1165, 49 (9).
Arnt et al. Facilitation of 8-OHDPAT-induced forepaw treading of rats by the 5-HT2 agonist DOI. Eur. J. Pharmacol., 161:45 (1989).
Barrett et al. Emotions and brain function are altered up to one month after a single high dose of psilocybin. Sci. Rep. 10:2214 (2020).
Belmaker et al. Major depressive disorder. N Engl J Med 358:55-68 (2008).
Billings et al. Social-environmental factors in unipolar depression; comparisons of depressed patients and nondepressed controls. J Abnormal Psychol 92:119-133 (1983).
Boulenguez et al. Modulation of dopamine release in the nucleus accumbens by 5-HT1E1 agonists: involvement of the hippocampo-accumbens pathway. Neuropharmacology 35:1521-1529 (1996).
Brun et al. Place cells and place recognition maintained by direct entorhinal-hippocampal circuitry. Science 296:2243-2246 (2002).
Burgdorf et al. Extinction of contextual cocaine memories requires Ca(v)1.2 within D1R-expressing cells and recruits hippocampal Ca(v)1,2-dependent signaling mechanisms. J Neurosci 37:11894-11911 (2017).
Burmeister et al. Differential roles of 5-HT receptor subtypes in cue and cocaine reinstatement of cocaine-seeking behavior in rats. Neuropsychopharmacology 29:660-668 (2004).
Cai et al. Local potentiation of excitatory synapses by serotonin and its alteration in rodent models of depression. Nat Neurosci 16:464-472 (2013).
Canal et al. Head-twitch response in rodents induced by the hallucinogen 2,5-dimethoxy-4-iodoamphetamine: a comprehensive history, a re-evaluation of mechanisms, and its utility as a model. Drug Test Anal., 4:556-576 (2012).
Canel et al. Support for 5-HT2C receptor functional selectivity in vivo utilizing structurally diverse, selective 5-HT2C receptor ligands and the 2,5-dimethoxy-4-iodoamphetamine elicited head-twitch response model. Neuropharmacol 70:112-121 (2013).
Carhart-Harris et al. Psilocybin for treatment-resistant depression: fMRI-measured brain mechanisms. Sci. Rep. 7:13187 (2017).
Carhart-Harris et al.: Psilocybin with psychological support for treatment-resistant depression: an open-label feasibility study. Lancet Psychiatry 3: 619-627. Published Online May 17, 2016 (2016).
Carhart-Harris et al.: Psilocybin with psychological support for treatment-resistant depression: six-month follow-up. Psychopharmacology (Berl). 235(2):399-408 doi:10.1007/s00213-017-4771-x (2018).
Carr et al. The role of serotonin receptor subtypes in treating depression: a review of animal studies, Psychopharmacology (Berl.) 213:265-287 (2011).

(56) References Cited

OTHER PUBLICATIONS

Chan et al. Strained in Planning Your Mouse Background? Using the HPA Stress Axis as a Biological Readout for Backcrossing Strategies. Neuropsychopharmacology 42:1749-1751 (2017).
Compass Pathways. Compass Pathways Receives FDA Breakthrough Therapy Designation for Psilocybin Therapy for Treatment-resistant Depression. Available at https://www.prnewswire.com/news-releases/compass-pathways-receives-fda-breakthrough-therapy-designation-for-psilocybin-therapy-for-treatment-resistant-depression-834088100.html (Oct. 23, 2018).
Co-pending U.S. Appl. No. 17/940,950, inventor Thompson; Scott, filed Sep. 8, 2022.
Co-pending U.S. Appl. No. 17/945,865, inventor Clark; Sam, filed Sep. 15, 2022.
Darmani et al., Do functional relationships exist between 5-HT1A and 5-HT2 receptors?. Pharmacol. Biochem. Behav., 36:901-606 (1990).
Dolen et al. Social reward requires coordinated activity of nucleus accumbens oxytocin and serotonin. Nature 501:179-184 (2013).
Drysdale et al. Resting-state connectivity biomarkers define neurophysiological subtypes of depression. Nature Med 23:28-38 (2017).
Duman et al. Altered connectivity in depression: GABA and glutamate neurotransmitter deficits and reversal by novel treatments. Neuron 102:75-90 (2019).
Engel et al. Identity of inhibitory presynaptic 5-hydroxytryptamine (5-1-IT) autoreceptors in the rat brain cortex with 5-HT1B binding sites Naunyn Schmiedebergs Arch Pharmacol 332:1-7 (1986).
Evans et al. Default mode connectivity in major depressive disorder measured up to 10 days after ketamine administration. Biol Psychiatry 84:582-590 (2018).
Fava et al. Major depressive disorder. Neuron 28:335-341 (2000).
Furay et al. 5-HT1B mRNA expression after chronic social stress. Behav Brain Res 224:350-357 (2011).
Gaynes et al. What did STAR*D teach us? Results from a large-scale, practical, clinical trial for patients with depression. Psychiart Serv. 60:1439-1445 (2009).
Gerfen et al. D1 and D2 dopamine receptor-regulated gene expression of striatonigral and striatopallidal neurons. Science 250(4986):1429-1432 (1990).
Gothert et al. Classification of serotonin receptors. J Cardiovasc Pharmacol 10 Suppl 3:S3-S7 (1987).
Halberstadt et al. Multiple receptors contribute to the behavioral effects of indoleamine hallucinogens. Neuropharmacol 61:364-381 (2011).
Hamet et al. Genetics and genomics of depression. Metabolism 54:10-15 (2005).
Hasler et al.: Determination of psilocin and 4-hydroxyindole-3-acetic acid in plasma by HPLC-ECD and pharmacokinetic profiles of oral and intravenous psilocybin in man. Pharm Acta Helv. 72(3):175-184 (1997).
Hibicke et al. Psychedelics, but Not Ketamine, Produce Persistent Antidepressant-like Effects in a Rodent Experimental System for the Study of Depression. ACS Chem Neurosci. 11(6):864-871 (2020).
Hoyer et al. International Union of Pharmacology classification of receptors for 5-hydroxytryptamine (Serotonin). Pharmacol Rev 46:157-203 (1994).
Jefsen et al. Psilocybin lacks antidepressant-like effect in the Flinders Sensitive Line rat. Acta Neuropsychiatr. 31:213-219 (2019).
Johnson et al. The abuse potential of medical psilocybin according to the 8 factors of the Controlled Substances Act. Neuropharmacology 142:143-166 (2018).
Kallarackal et al. Chronic stress induces a selective decrease in AIVIPA receptor-mediated synaptic excitation at hippocampal temporoammonic-CA1 synapses. Neurosci 33:15669-15674 (2013).
Keller et al. Permanent alteration of behavior in mice by chemical and psychological means. Science 124:723 (1956).
Kennett et al., In vivo properties of SB 200646A, a 5-HT2C/2B receptor antagonist. J. Pharmacol., 111:797-802 (1994).
Kessler et al. Lifetime prevalence and age-of-onset distributions of DSM-IV disorders in the National Comorbidity Survey Replication. Arch Gen Psychiatry 62:593-602 (2005).
Kessler, et al. The epidemiology of major depressive disorder: results from the National Comorbidity Survey Replication (NCS-R). JAMA. Jun. 18, 2003;289(23):3095-105.
Lee et al. Specific roles of AMPA receptor subunit GluR1 (GluA1) phosphorylation sites in regulating synaptic plasticity in the CA1 region of hippocampus. J Neurephysiol 103:479-489 (2010).
Legates et al. Reward behaviour is regulated by the strength of hippocampus-nucleus accumbens synapses. Nature 564:258-262 (2018).
Legates et al. Sex differences in antidepressant efficacy. Neuropsychopharmacol 44:140-154 (2019).
Li et al. Synaptic potentiation onto habenula neurons in the learned helplessness model of depression. Nature 470:535-539 (2011).
Lim et al. Anhedonia requires MC4R-mediated synaptic adaptations in nucleus act umbens. Nature 87:183-189 (2012).
Ly et al., Psychedelics promote structural and functional neural plasticity. Cell Rep. 23(11):3170-3182 (2018).
Madsen et al.: Psychedelic effects of psilocybin correlate with serotonin 2A receptor occupancy and plasma psilocin levels. Neuropsychopharmacology 44(7):1328-1334 (2019).
Mathur et al. Serotonin induces long-term depression at corticostriatal synapses. J Neurosci 31:7402-7411 (2011).
Maura et al. Serotonin autoreceptor in rat hippocampus: pharmacological characterization as a subtype of the 5-HT1 receptor. Naunyn Schmiedebergs Arch Pharmacol 334:323-326 (1986).
McEwen. Stress and hippocampal plasticity. Ann Rev Neurosci 22:105-122 (1999).
Moda-Sava et al. Sustained rescue of prefrontal circuit dysfunction by antidepressant-induced spine formation. Science 364(6436):eaaat8078 (2019).
Nautiyal et al. Distinct circuits underlie the effects of 5-HT1B receptors on aggression and impulsivity. Neuron 86:813-826 (2015).
Nestler, et al. Neurobiology of depression. Neuron. Mar. 28, 2002;34(1):13-25.
Nestler et al. The mesolimbic dopamine reward circuit in depression. Biol Psychiatry 59:1151-1159 (2006).
Neumaier et al. Chronic fluoxetine reduces serotonin transporter mRNA and 5-HT1B mRNA in a sequential manner in the rat dorsal raphe nucleus. Neuropsychopharmacology 15:515-522 (1996).
Nichols. Psychedelics. Pharmacol Rev. 68:264-35 (2016).
Nutt et al. Independent Scientific Committee on Drugs. Drug harms in the UK: a multicriteria decision analysis. Lancet 376:1558-1565 (2010).
Nutt et al. Psychedelic Psychiatry's Brave New World. Cell 181:24-28 (2020).
PCT/EP2018/079503 International Search Report and Written Opinion dated Feb. 1, 2019.
PCT/US2020/046149 International Search Report and Written Opinion dated Jan. 11, 2021.
PCT/US2022/023067 International Search Report and Written Opinion dated Jun. 21, 2022.
Remondes et al. Role for a cortical input to hippocampal area CA1 in the consolidation of a long-term memory. Nature 431:699-703 (2004).
Roseman et al. Quality of Acute Psychedelic Experience Predicts Therapeutic Efficacy of Psilocybin for Treatment-Resistant Depression Front. Pharmacol. 8:974 (2018).
Roth et al. Serotonin 5-HT2A receptors: molecular biology and mechanisms of regulation. Crit Rev. Neurobiol 12:319-338 (1998).
Svenningsson et al. Alterations in 5-HT(1B) receptor function by p11 in depression-like states. Science 311:77-80 (2006).
Thompson et al. An excitatory synapse hypothesis of depression. Trends Neurosci 38:279-294 (2015).
Tye et al. Dopamine neurons modulate neural encoding and expression of depression-related behaviour. Nature 493:537-541 (2013).
Van Dyke et al. Chronic fluoxetine treatment in vivo enhances excitatory synaptic transmission in the hippocampus. Neumpharmacology 150:38-45 (2019).
Weisstaub et al. Cortical 5-HT2A receptor signaling modulates anxiety-like behaviors in mice. Science 313:536-540 (2006).

(56) References Cited

OTHER PUBLICATIONS

Willner. The chronic mild stress (CMS) model of depression: History, evaluation and usage. Neurobiol Stress 6:78-93 (2016).
Winter et al. Psilocybin-induced stimulus control in the rat. Pharmacol Biochem Behav. 87:472-480 (2007).
Yuen et al. Repeated stress causes cognitive impairment by suppressing glutamate receptor expression and function in prefrontal cortex. Neuron 73:962-977 (2012).

* cited by examiner

A

B

A) DMT

B) DET, DPT and 5-MeO-DMT

A)

B)

COMBINATION PRODUCT FOR THE TREATMENT OF NEUROLOGICAL AND/OR PSYCHIATRIC DISORDERS

TECHNICAL FIELD

The present invention relates to a novel pharmaceutical combination product. The combination product and its components may be used as a medicament, in particular, as a medicament for the treatment and/or prevention of neurological and/or psychiatric disorders.

BACKGROUND ART

Adult neurogenesis is defined as the process of generating functional neurons from neural stem cells (Gage, 2000. *Science.* 287 (5457): 1433-8) (Temple, 2001. *Nat. Rev. Neurosci.* 2 (7): 513-20). These newly generated neurons have the capacity to migrate and integrate into existing neural circuits. Stimulating neurogenesis has been proposed as a new therapeutic strategy for psychiatric and neurologic disorders (Herrera-Arozamena et al., 2016. *Molecules.* 21 (9): E1165). Moreover, clinical efficacy of antidepressants is linked to a drug's capacity to induce neurogenesis (Chen et al., 2007. *Curr. Neurovasc. Res.* 4 (1): 19-29; Boldrini et al., 2009. *Neuropsychopharmacology.* 34 (11): 2376-89; Sachs and Caron, 2015. *Int. J. Neuropsychopharmacol.* 18 (4)).

N,N-dimethyltryptamine (DMT) is a natural compound found in numerous plant species and botanical preparations such as the hallucinogenic tea ayahuasca (Riba et al., 2003, *J. Pharmacol. Exp. Ther* 306 (1): 73-83). DMT is classified as a hallucinogen or psychedelic, inducing intense modifications in perception, emotion, cognition and volition when given to humans (Strassmann et al., 1994, *Arch. Gen Psychiatry* 51 (2): 98-108). DMT has long been known to bind and display agonist activity at serotonin (5-HT) receptor subtypes 2A (5-HT2A) and 1A (5-HT1A) (McKenna et al., 1990. *Neuropharmacology.* 29 (3): 193-198). More recent studies have shown that DMT also binds with lower affinity to non-serotonergic receptors, such as the trace amine-associated receptor (Rickli et al., 2016. *Eur Neuropharmacol.* 26 (8): 1327-1337), and the Sigma-1 receptor (Fontanilla et al., 2009. *Science.* 323 (5916): 934-7). Despite its interaction with various molecular targets, the hallucinogenic or psychedelic effects of DMT are believed to be caused by the drug's activation of the 5-HT2A receptor (Nichols, 2004. *Pharmacol. Ther.* 101 (2): 131-81). As shown experimentally, administration of the 5-HT2A receptor antagonist ketanserin, counteracts the hallucinogenic effects of the DMT-containing preparation ayahuasca in humans (Valle et al., 2016. *Eur Neuropharmacol.* 26 (7): 1161-1175).

The fact that DMT binds and regulates the Sigma-1 receptor (Fontanilla et al., 2009. *Science.* 323 (5916): 934-7) is of special interest. The Sigma-1 receptor has been associated with several cellular functions, including: lipid transport and calcium signaling between the endoplasmic reticulum and mitochondria (Hayashi and Su, 2007. *Cell.* 131 (3): 596-610), stress-response signaling (Mori et al., 2013. *PLoS ONE.* 8 (10): e76941), protecting the cell against oxidants (Pal et al., 2012. *Eur. J. Pharmacol.* 682 (1-3): 12-20), suppressing apoptosis (Omi et al., 2014. *Cell Death Dis.* 5: e1332) and immunomodulatory functions (Szabo et al., 2014. *PLoS ONE.* 9 (8): e106533). The Sigma-1 receptor may also be a potential target for treating neurodegenerative diseases and stroke (Ruscher & Wieloch, 2015. *J. Pharmacol. Sci.* 127(1):30-5).

Various authors have proposed the use of ayahuasca or DMT alone as a possible medicament for the treatment of psychiatric and/or neurological disorders (Szabo and Frecksa, 2016. *Neural Regen. Res.* 11 (3): 396-7; Frecksa et al., 2016. *Front. Pharmacol.* 7: 35; Szabo et al., 2016. *Front. Neurosci.* 10:423). Moreover, the efficacy of ayahuasca preparations to treat depression has been demonstrated (Osório et al., 2015. *Revista Brasileira de Psiquiatria.* 37 (1): 13-20). However, the capacity of DMT to stimulate neurogenesis has not been assessed. Moreover, DMT itself and DMT-containing preparations such as ayahuasca cause hallucinogenic or psychedelic side effects that constitute a serious limitation for the use of DMT or DMT-containing preparations for therapeutic purposes. Analogous hallucinogenic side effects are observed for other N-alkylated tryptamines such as N,N-diethyltryptamine, N,N-dipropyltryptamine, 5-methoxy-N,N-dimethyltryptamine, or psilocybin (4-Phosphoryloxy-N,N-dimethyltryptamine), among others (Tittarelli et al., 2015. *Current Neuropharmacol.* 13: 26-46). All these compounds show structure and receptor affinity profiles that are closely related to those of DMT (Ray, 2010. *PLoS ONE.* 5(2): e9019; Tittarelli et al., 2015. *Current Neuropharmacol.* 13: 26-46). As observed for the DMT-containing preparation ayahuasca, blocking the 5-HT2A receptor with ketanserin also prevents the hallucinogenic effects of psilocybin (Vollenweider et al., 1998. *Neuroreport.* 9 (17): 3897-3902) and LSD (lysergic acid diethylamide; Preller et al., 2017. *Curr. Biol.* 27 (3): 451-457) in humans. These results further support activation of the 5-HT2A receptor as the underlying mechanism responsible for the side effects of hallucinogenic tryptamines.

The prior art does not disclose a pharmaceutical combination product comprising the components of the present invention. In Valle et al., 2016. *Eur Neuropharmacol.* 26 (7): 1161-1175 ketanserin is administered to study the effects of 5-HT2A receptor activation in the neurophysiological and visual effects of ayahuasca in humans (see abstract). In Kometer et al., 2012. *Biol Psychiatry.* 72(11):898-906 ketanserin was administered to study the effects of 5-HT2A receptor activation on mood regulation and emotional face recognition (see abstract). In Tylš et al., 2016. *Behav Pharmacol.* 27(4):309-20 MDL100908 was administered to study the effects of sex-specific reactions to serotonergic receptor activation. Thus, none of these documents disclose a hallucinogenic or psychedelic tryptamine and a 5-HT2A receptor antagonist in a single pharmaceutical combination product for use as a medicament as defined in the present application.

There is currently a need for a combination product that can be used to treat and/or prevent neurological and/or psychiatric disorders by taking advantage of the beneficial effects of DMT and/or other hallucinogenic tryptamines, but avoiding their undesired side effects. The goal of the present invention is to provide such a combination product.

FIGURES

FIG. 1: DMT administration in vitro reduces the levels of protein markers of the undifferentiated state (i.e., "stemness") of adult neural stem cells derived from the subgranular zone of the hippocampus through interaction with the Sigma-1 receptor. This desired effect is maintained in the presence of 5-HT2A antagonists. Bar graphs showing quantification of the protein levels of the precursor cell markers musashi-1, nestin and SOX-2 after treatment with DMT (1 μM). Specific cultures were previously treated with either the selective Sigma-1 receptor antagonist BD1063 (BD, 1

µM), the mixed serotonin 5-HT1A/2A receptor antagonist Methiothepin (Met, 1 µM), the selective 5-HT2A receptor antagonist Ritanserin (Rit, 1 µM), or the selective 5-HT1A receptor antagonist WAY100635 (WAY, 1 µM) 1 h prior to DMT addition. Bar graphs show relative protein levels. Values indicate mean±SEM from three independent experiments. **p≤0.01 versus saline-treated (basal) cultures. DMT effects were preserved in the presence Met, Rit and WAY, but not in the presence of BD. These results illustrate: a) The novel and unexpected finding that DMT reduces the undifferentiated state or "stemness" of neural progenitor cells; b) The novel and unexpected finding that DMT reduces "stemness" by stimulating the Sigma-1 receptor; c) The novel and unexpected finding that DMT-induced reductions in "stemness" are not mediated by the 5-HT1A receptor (WAY); d) The innovative finding that DMT-induced "stemness" reductions are preserved when this hallucinogenic tryptamine is combined with a mixed (Met) or selective (Rit) 5-HT2A antagonist. These results indicate that the desired effects of DMT are preserved when combined with a 5-HT2A antagonist. Since the latter blocks the side effects of hallucinogenic tryptamines in humans, the proposed drug combination would retain the desired therapeutic effects, while eliminating the undesired hallucinogenic effects.

Figure 2:
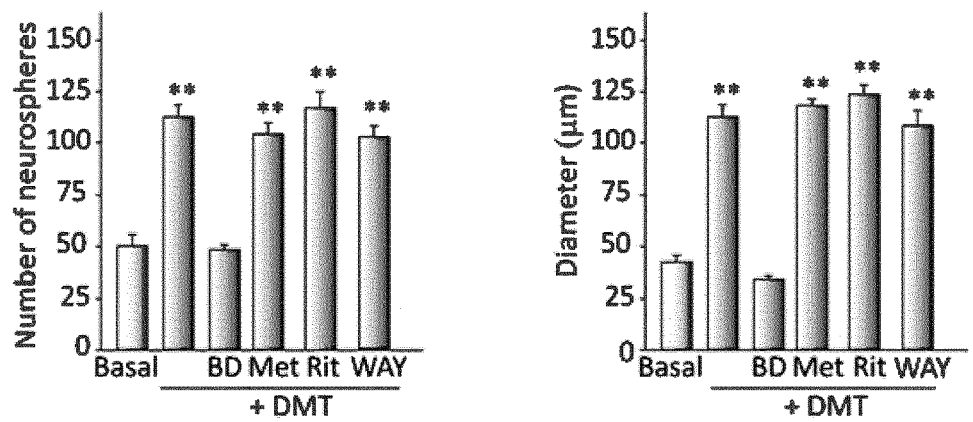

FIG. 2: DMT administration in vitro increases the number and size of neurospheres formed from cultured adult neural stem cells derived from the subgranular zone of the hippocampus through interaction with the Sigma-1 receptor. This desired effect is maintained in the presence of 5-HT2A antagonists. Quantification of the number and size of neurospheres after 7 days in culture in the presence of DMT (1 µM) alone or in combination with either BD1063 (BD, 1 µM), Methiothepin (Met, 1 µM), Ritanserin (Rit, 1 µM), or WAY100635 (WAY, 1 µM). The number and diameter of at least 50 neurospheres was determined in control and treated cultures. Bar graphs showing results as mean values±SEM from three independent experiments. **≤0.01 versus saline-treated (basal) cultures. DMT effects were preserved in the presence Met, Rit and WAY, but not in the presence of BD. These results illustrate: a) The novel and unexpected finding that DMT promotes the generation of neurospheres from neural progenitor cells; b) The novel and unexpected finding that DMT-induced increases in neurosphere formation (number and size) are mediated by stimulation of the Sigma-1 receptor; c) The novel and unexpected finding that DMT-induced increases in neurosphere formation are not mediated by the 5-HT1A receptor (WAY); d) The innovative finding that DMT-induced increases in neurosphere formation are preserved when this hallucinogenic tryptamine is combined with a mixed (Met) or selective (Rit) antagonist. These results indicate that the desired effects of DMT are preserved when combined with a 5-HT2A antagonist. Since the latter block the side effects of hallucinogenic tryptamines in humans, the proposed drug combination would retain the desired therapeutic effects, while eliminating the undesired hallucinogenic effects.

Figure 3:
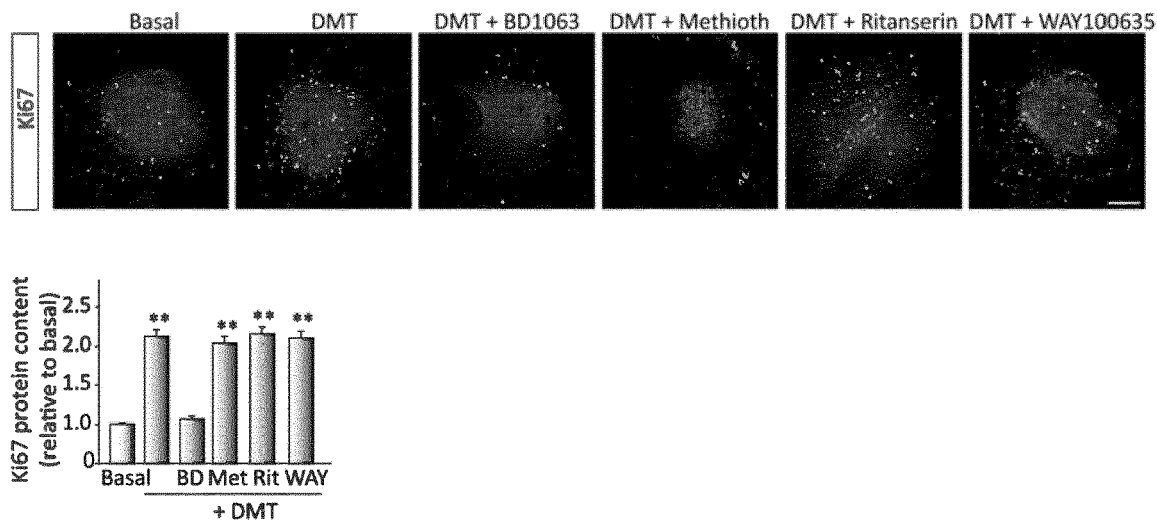

FIG. 3: DMT administration in vitro increases proliferation of cultured adult neural stem cells derived from the subgranular zone of the hippocampus through interaction with the Sigma-1 receptor. This desired effect is maintained in the presence of 5-HT2A antagonists. Top panel: Representative images showing the expression ki67 (white zones), a cellular marker for proliferation, in neurospheres treated with DMT (1 µM) alone or in combination with BD1063 (BD, 1 µM), Methiothepin (Met, 1 µM), Ritanserin (Rit, 1 µM) or WAY100635 (WAY, 1 µM) for 7 days. Scale bar=50 µm. Bottom panel: Quantification of ki67 protein levels in the neurospheres. Each bar indicates relative protein levels expressed as mean±SEM from three independent experiments. **p≤0.01 versus saline-treated (basal) cultures. DMT effects were preserved in the presence Met, Rit and WAY, but not in the presence of BD. These results illustrate: a) The novel and unexpected finding that DMT promotes the proliferation of neural progenitor cells; b) The novel and unexpected finding that DMT-induced increases in proliferation are mediated by stimulation of the Sigma-1 receptor; c) The novel and unexpected finding that DMT-induced increases in proliferation are not mediated by the 5-HT1A receptor (WAY); d) The innovative finding that DMT-induced increases in proliferation are preserved when this hallucinogenic tryptamine is combined with a mixed (Met) or selective (Rit) 5-HT2A antagonist. These results indicate that the desired effects of DMT are preserved when combined with a 5-HT2A antagonist. Since the latter block the side effects of hallucinogenic tryptamines in humans, the proposed drug combination would retain the desired therapeutic effects, while eliminating the undesired hallucinogenic effects.

Figure 4:
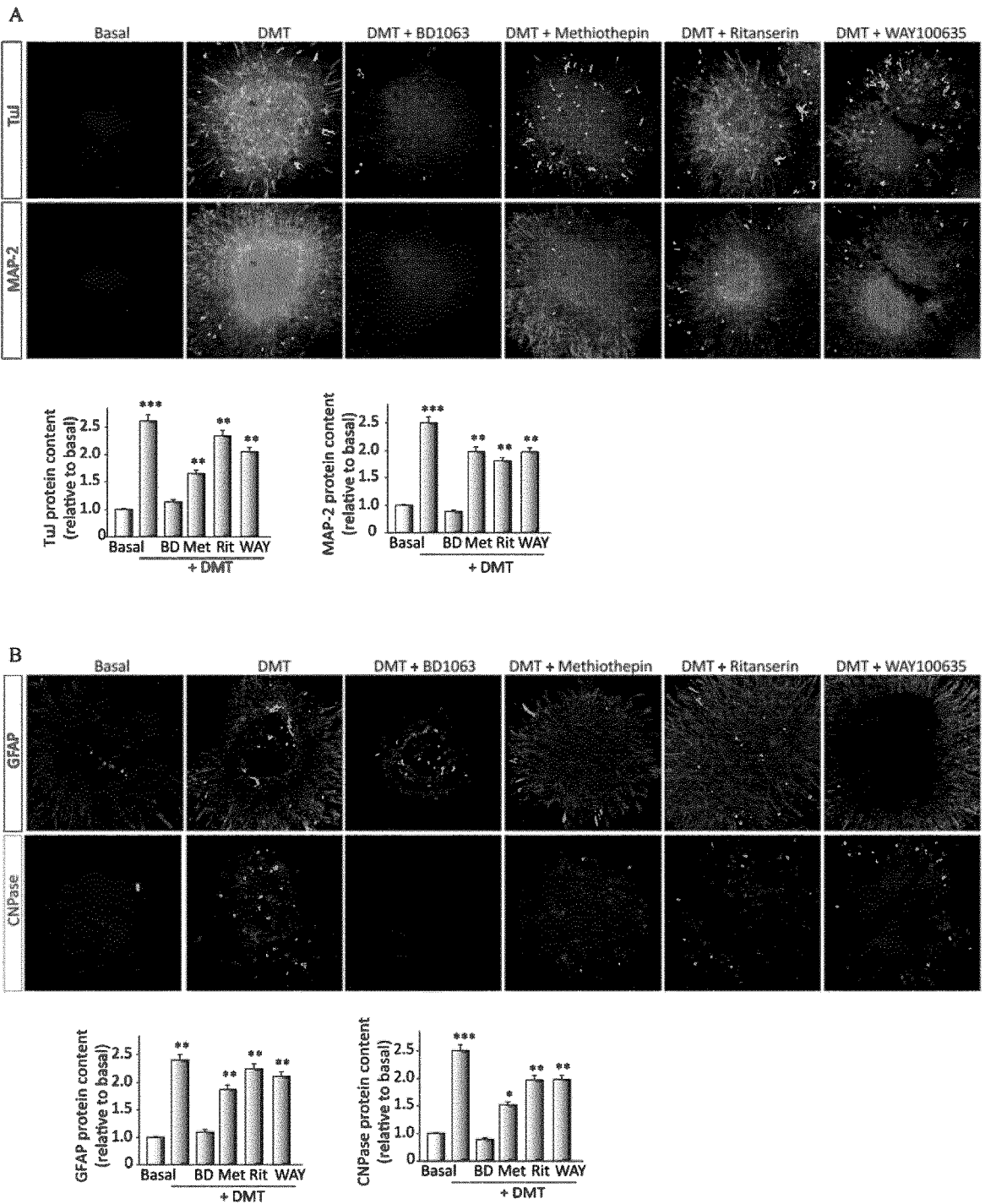

FIG. 4: DMT administration in vitro promotes the differentiation into neurons and glial cells of cultured adult neural stem cells derived from the subgranular zone of the hippocampus through interaction with the Sigma-1 receptor. This desired effect is maintained in the presence of 5-HT2A antagonists. After 7 days in culture in the presence of DMT alone or in combination with BD1063 (BD, 1 µM), Methiothepin (Met, 1 µM), Ritanserin (Rit, 1 µM), or WAY100635 (WAY, 1 µM), free floating neurospheres derived from the adult subgranular zone were adhered on coated coverslips and allowed to differentiate for 3 days in the presence of the drug combinations. A) Representative images showing the expression of the neuronal markers β-III-Tubulin (TuJ-1 clone) and MAP-2 in the neurospheres (white zones). Bar graphs show protein levels in each treatment condition. Each bar indicates relative protein levels expressed as mean±SEM from three independent experiments. *p≤0.001, p≤0.01 versus saline-treated (basal) cultures. B) Images showing the expression of CNPase (oligodendrocyte marker) and glial fibrillary acidic protein (GFAP) that stains astrocytes (white zones). Bar graphs show protein levels in each treatment condition. Each bar indicates relative protein levels expressed as mean±SEM from three independent experiments. *p≤0.001, p≤0.01, *p≤0.05 versus saline-treated (basal) cultures. DMT effects were preserved in the presence of Met, Rit or WAY, but not in the presence of BD. These results illustrate: a) The novel and unexpected finding that DMT promotes the differentiation of neural stem cells into neurons and glial cells; b) The novel and unexpected finding that DMT-induced differentiation is mediated by stimulation of the Sigma-1 receptor; c) The novel and unexpected finding that DMT-induced increases in differentiation are not mediated by the 5-HT1A receptor (WAY); d) The innovative finding that DMT-induced increases in differentiation are preserved when this hallucinogenic tryptamine is combined with a mixed (Met) or selective (Rit) 5-HT2A antagonist. These results indicate that the desired effects of DMT are preserved when combined with a 5-HT2A antagonist. Since the latter block the side effects of hallucinogenic tryptamines in humans, the proposed drug combination would retain the desired therapeutic effects, while eliminating the undesired hallucinogenic effects.

Figure 5:
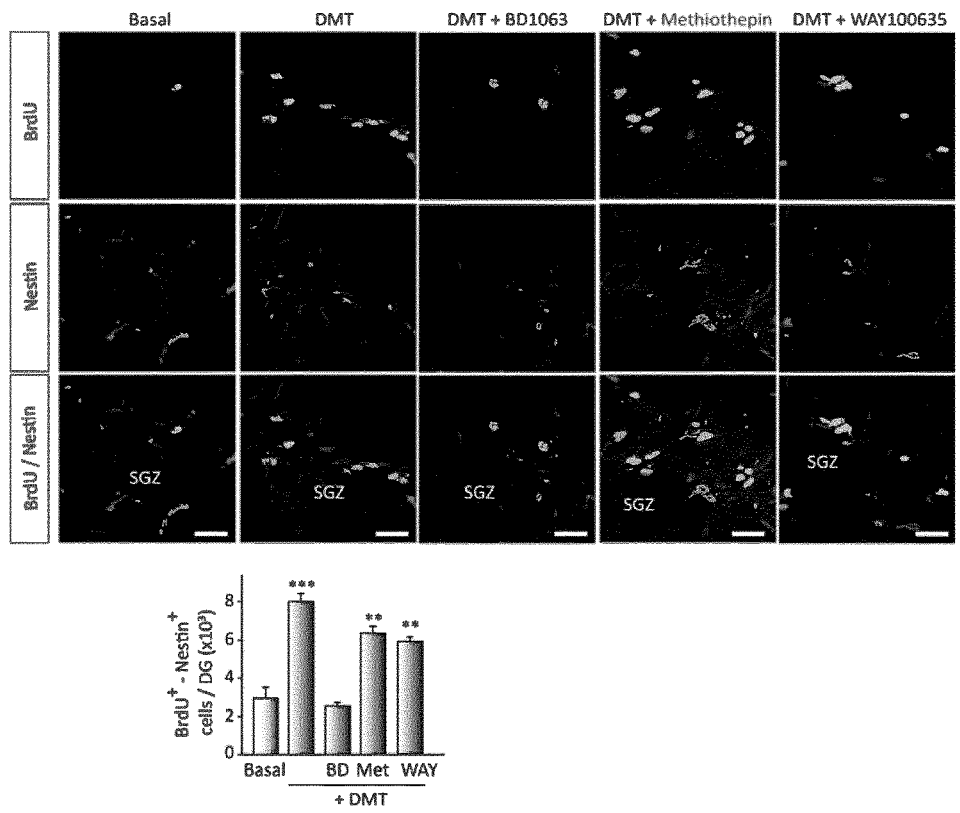
Figure 5:
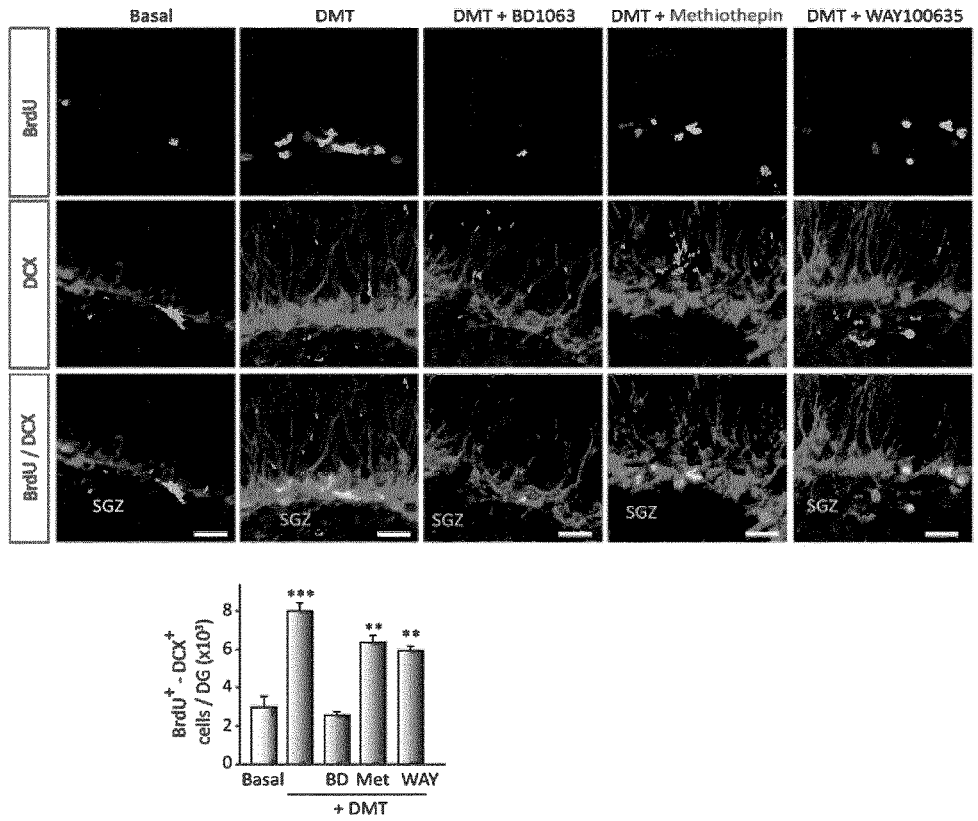

FIG. 5: DMT administration in vivo activates the hippocampal subgranular neurogenic niche in live mice through interaction with the Sigma-1 receptor. This desired effect is maintained in the presence of a mixed 5-HT2A/1A antagonist and is not influenced by DMT-induced 5-HT1A stimulation. Short-term study (4 days) Adult mice were intraventricularly injected with 0.1 µg DMT alone or in combination with either 0.2 µg BD1063 (BD), 0.2 µg Methiothepin (Met) or 0.2 µg WAY100635 (WAY). After 4 days, animals were intraperitoneally injected with 5-bromo-2-deoxyuridine (BrdU, 50 mg/kg) and sacrificed on day 5. A) Representative images of coronal brain sections showing in white the expression of BrdU (a proliferation marker) and Nestin (a marker of neural progenitor cells) in the hippocampus. Scale bar: 50 µm (×20 magnification). The bar graph shows the quantification of the double stained Brdu-Nestin cells through the entire dentate gyrus (DG) after each treatment. *$p \leq 0.001$, $p \leq 0.01$ versus vehicle-treated (basal) cultures. B) Representative images of coronal brain sections showing in white the expression of BrdU (a proliferation marker) and DCX (a migrating neuroblasts marker) in the hippocampus. Scale bar: 50 µm (×20 magnification). The bar graph shows the quantification of the double stained Brdu-DCX cells through the entire dentate gyrus (DG) in each treatment condition. *$p \leq 0.001$, $p \leq 0.01$ versus vehicle-treated (basal) cultures. DMT effects were preserved in the presence of Met and WAY, but not in the presence of BD. These results illustrate: a) The novel and unexpected finding that DMT stimulates the hippocampal neurogenic niche in live animals; b) The novel and unexpected finding that DMT-induced stimulation of the hippocampal neurogenic niche in vivo is mediated via the Sigma-1 receptor; c) The novel and unexpected finding that DMT-induced stimulation of the hippocampal neurogenic niche in vivo is not mediated by the 5-HT1A receptor (the effects were preserved in the presence of the mixed 5-HT2A/1A receptor antagonist methiothepin and in the presence of the selective 5-HT1A receptor antagonist WAY100635); d) The innovative finding that the DMT-induced stimulation of the hippocampal neurogenic niche in vivo is preserved when this hallucinogenic tryptamine is combined with a 5-HT2A antagonist (in this example the mixed 5-HT2A/1A receptor antagonist methiothepin), and that this effect is not mediated by the 5-HT1A receptor. Since 5-HT2A antagonists block the side effects of hallucinogenic tryptamines in humans, the proposed drug combination would retain the desired therapeutic effects, while eliminating the undesired hallucinogenic effects. Further, the therapeutic effect is still obtainable even if the 5-HT2A antagonist is not completely selective and displays 5-HT1A antagonism.

Figure 6:
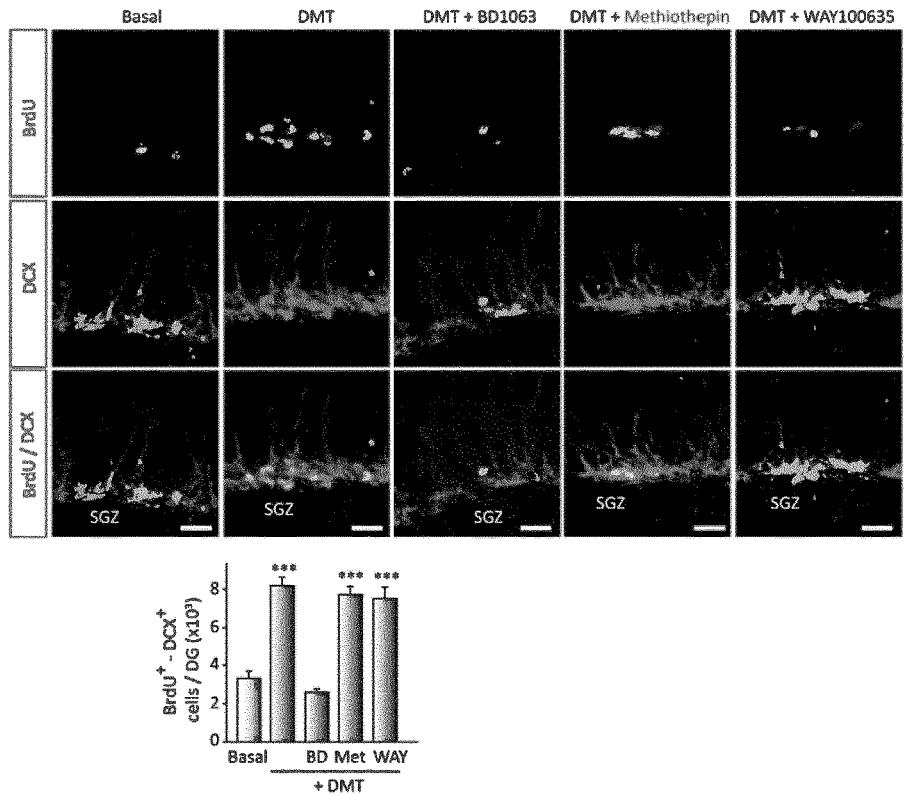
Figure 6:
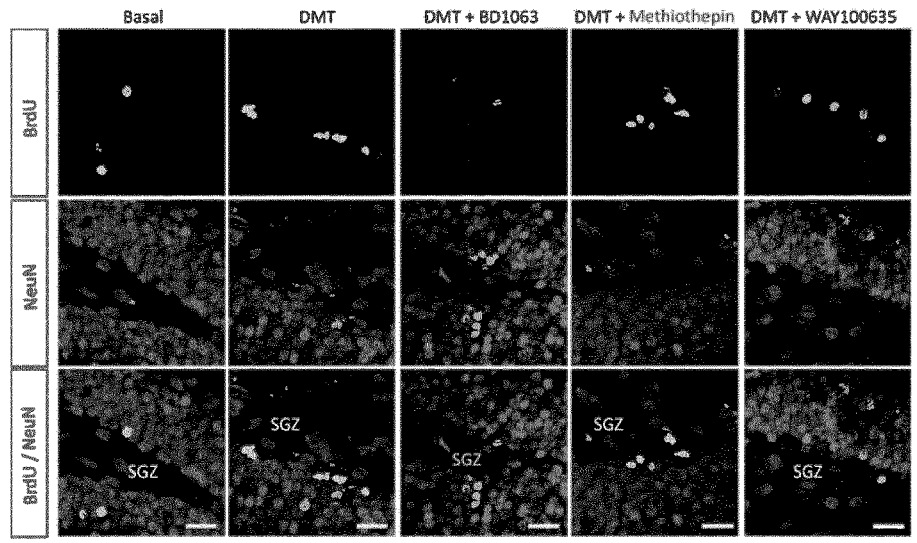

FIG. 6: DMT administration promotes in vivo neurogenesis in the subgranular zone of the hippocampus in live mice through interaction with the Sigma-1 receptor. This desired effect is maintained in the presence of a mixed 5-HT2A/1A antagonist and does not depend on 5-HT1A stimulation by DMT. Long-term experiment (21 days). Adult mice were intraperitoneally injected with 0.1 µg DMT alone or in combination with either 0.2 µg BD, 0.2 µg Met, or 0.2 µg WAY every other day for 3 weeks. On day 1 animals were intraperitoneally injected with 5-bromo-2-deoxyuridine (BrdU, 50 mg/kg) and sacrificed on day 21. A) Representative confocal images of coronal brain sections showing in white the expression of BrdU (a proliferation marker) and DCX (a migrating neuroblasts marker) in the subgranular zone of the hippocampus. Scale bar: 20 µm (×63 magnification). DMT effects were preserved in the presence of Met and WAY, but not in the presence of BD. The bar graph shows the number of cells showing dual BrdU/DCX positive staining throughout the entire DG in each treatment condition. Each bar indicates the number of cells expressed as mean±SEM from three independent experiments. *$p \leq 0.001$ versus vehicle-treated (basal) animals. B) Representative confocal images of coronal brain sections showing in white against black background the expression of BrdU (a proliferation marker) and NeuN (a neuronal marker) in the subgranular zone of the hippocampus. Scale bar: 20 µm (×63 magnification). DMT effects were preserved in the presence of Met and WAY, but not in the presence of BD. The bar graph shows the number of cells showing dual BrdU$^+$/NeuN$^+$ positive staining in each treatment condition. Cells showing dual staining are newly generated neurons. Each bar indicates number of cells expressed as mean±SEM from three independent experiments. $p \leq 0.01$ versus vehicle-treated (basal) animals. Note that after 5 days of DMT administration, the number of newly generated neurons has doubled as compared to basal. Neurogenic effects are abolished by BD but not by Met or WAY. These results illustrate: a) The novel and unexpected finding that DMT stimulates the hippocampal neurogenic niche and promotes neurogenesis in vivo in adult live animals, i.e., the differentiation of hippocampal neural progenitors into a neuronal phenotype; b) The novel and unexpected finding that DMT-induced in vivo hippocampal neurogenesis is mediated via the Sigma-1 receptor; c) The novel and unexpected finding that DMT-induced in vivo hippocampal neurogenesis is not mediated by the 5-HT1A receptor (the effects were preserved in the presence of the mixed 5-HT2A/1A receptor antagonist methiothepin and in the presence of the selective 5-HT1A receptor antagonist WAY100635); d) The innovative finding that DMT-induced in vivo hippocampal neurogenesis is preserved when this hallucinogenic tryptamine is combined with a 5-HT2A antagonist (in this example the mixed 5-HT2A/1A receptor antagonist methiothepin) and that this effect is not mediated by the 5-HT1A receptor. Since 5-HT2A antagonists block the side effects of hallucinogenic tryptamines in humans, the proposed drug combination would retain the desired therapeutic effects, while eliminating the undesired hallucinogenic effects. Further, the therapeutic effect is still obtainable even if the 5-HT2A antagonist is not completely selective and displays 5-HT1A antagonism.

Figure 7:
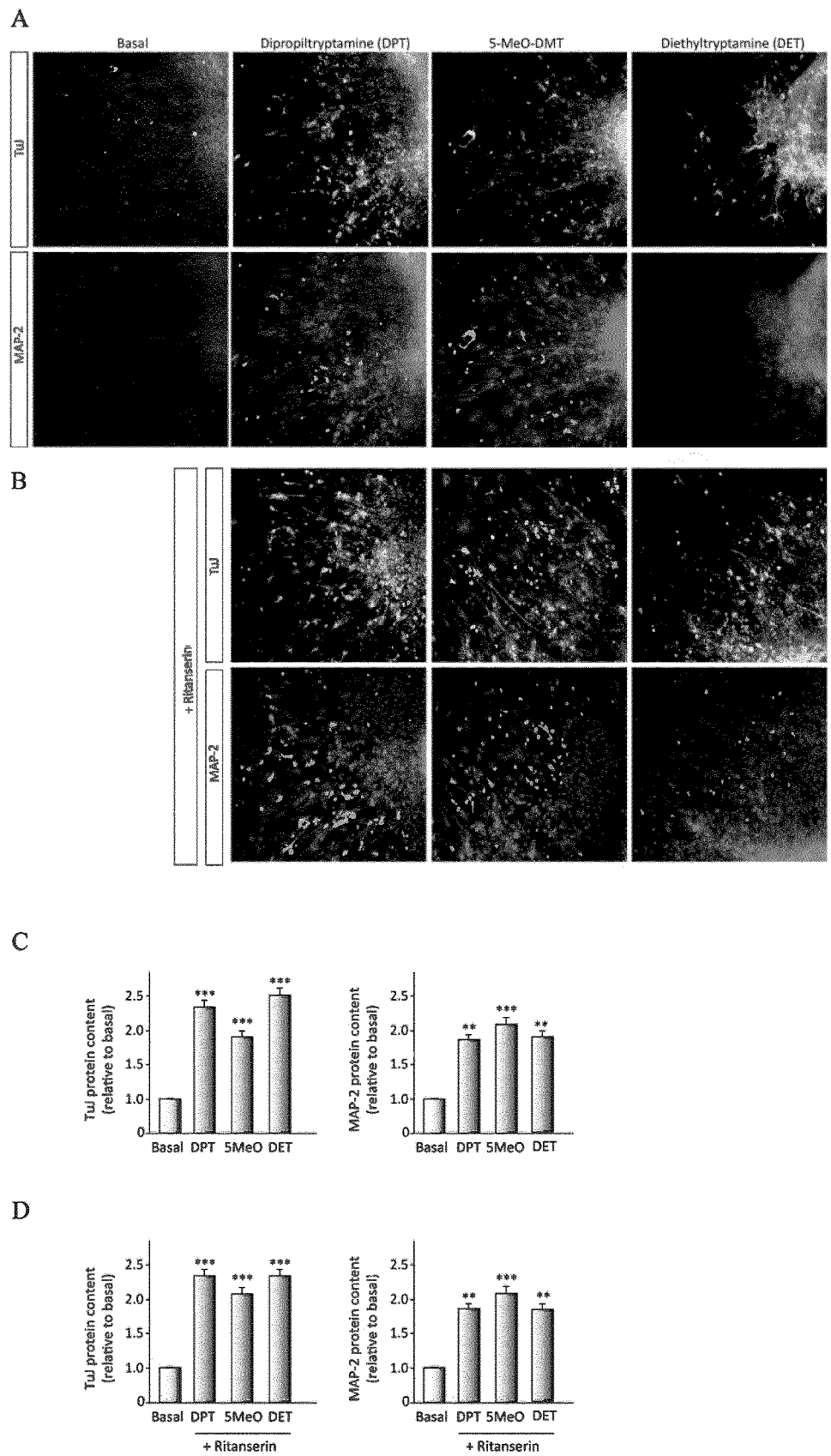

FIG. 7: Administration of the hallucinogenic tryptamines N,N-dipropyltryptamine (DPT), 5-methoxy-N,N-dimethyltryptamine (5-MeO-DMT) and N,N-diethyltryptamine (DET) in vitro promote the differentiation into neurons of cultured adult neural stem cells derived from the subgranular zone of the hippocampus. This desired effect is maintained in the presence of a selective 5-HT2A antagonist. After 7 days in culture in the presence of 1 µM DPT, DET or 5-MeO-DMT alone, or after pre-treatment with the selective 5-HT2A antagonist ritanserin (Rit, 1 µM), free floating neurospheres derived from the adult subgranular zone were adhered on coated coverslips and allowed to differentiate for 3 days in the presence of the drugs. A) Representative images showing the expression of the neuronal markers β-III-Tubulin (TuJ-1 clone) and MAP-2 in the neurospheres (white zones) after treatment with each tryptamine at 1 µM. B) Representative images showing the expression of the neuronal markers β-III-Tubulin (TuJ-1 clone) and MAP-2 in the neurospheres (white zones) pretreated for 1 h with the selective 5-HT2A antagonist ritanserin (1 µM) and later treated by the different tryptamines at 1 µM. C) Bar graphs show protein levels in each treatment condition. Each bar indicates relative protein levels expressed as mean±SEM from three independent experiments. *$p \leq 0.001$, $p \leq 0.01$ versus saline-treated (basal) cultures. D) Bar graphs indicate protein levels depicted as images in panel B, where neurospheres were first pretreated with Rit before tryptamines were added to the culture. Each bar indicates relative protein levels expressed as mean±SEM from three independent experiments. *p≤0.001, p≤0.01 versus saline-treated (basal) cultures. In panels C and D 5-MeO-DMT appears indicated by the abbreviation "5MeO". As shown in the images and graphs, all three tryptamines promoted differentiation of neural stem cells into neurons. This effect was not affected by a co-treatment with Rit. No statistically significant differences were found in protein levels between cultures treated with each tryptamine alone and cultures treated with the tryptamine+Rit combination. These results illustrate: a) The novel and unexpected finding that the hallucinogenic tryptamines DPT, 5-MeO-DMT, and DET promote the differentiation of neural stem cells into neurons; b) That the neurogenic effects previously demonstrated for DMT are not exclusive to this compound, but extend to other hallucinogenic tryptamines as well; c) The innovative finding that the differentiation into neurons is unaffected by the presence of a 5-HT2A antagonist. Since 5-HT2A antagonists block the side effects of hallucinogenic tryptamines in humans, the proposed drug combination would retain the desired therapeutic effects, while eliminating the undesired hallucinogenic effects.

Figure 8:
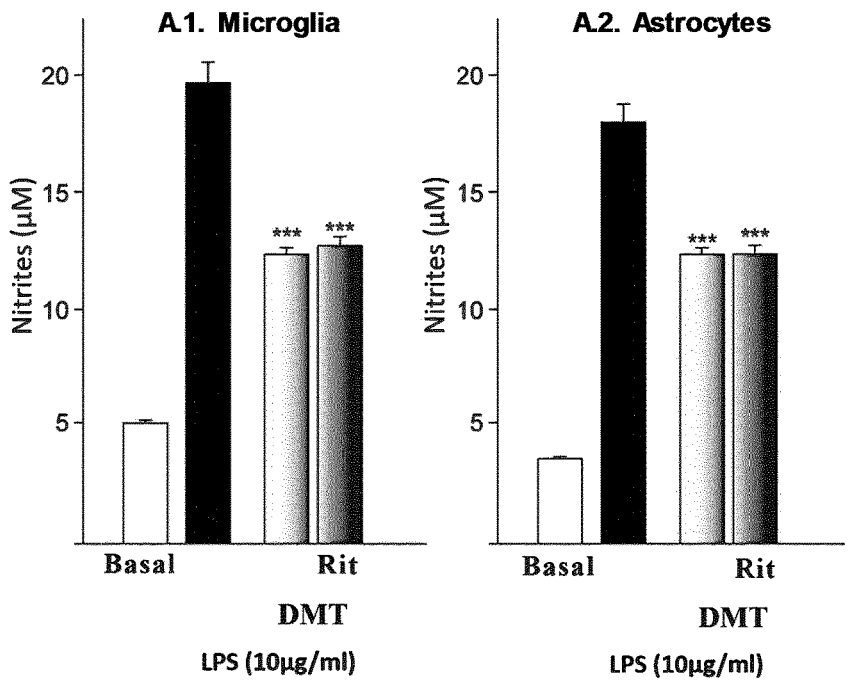
Figure 8:
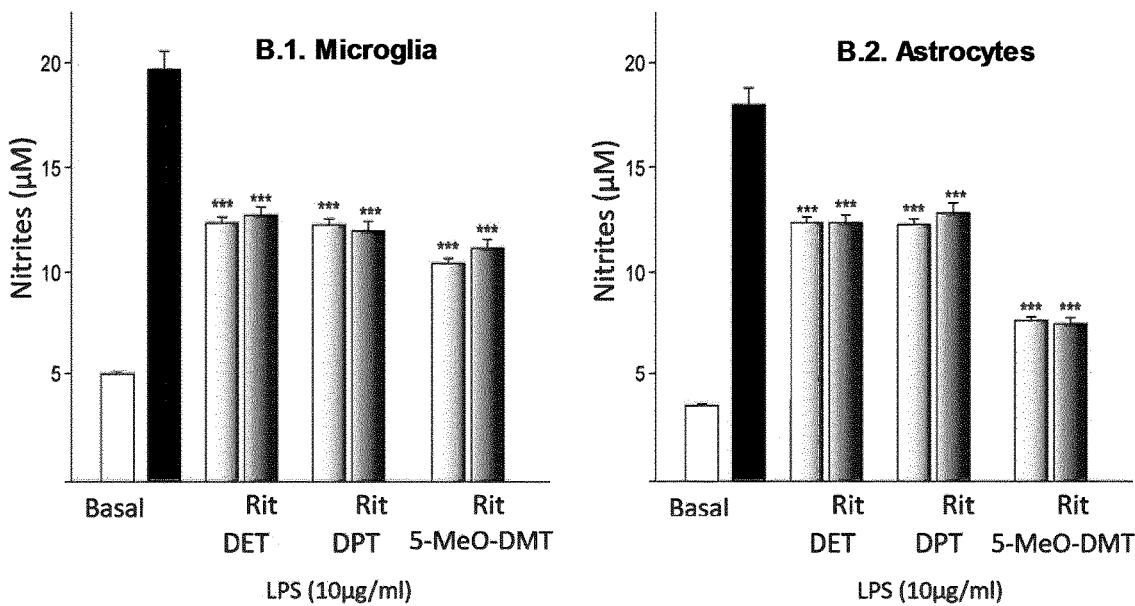

FIG. 8: DMT, DET, DPT and 5-MeO-DMT administration in vitro prevents inflammation in cultured glial cells. All compounds prevented the inflammatory response elicited by lipopolysaccharide (LPS; 10 μg/mL). These beneficial effects were obtained using the same trytamine concentration (1 μM) found to promote adult neurogenesis in vitro, as shown in previous examples (see FIGS. 1 to 4 and FIG. 7). Nitrite production, an indicator of active inflammatory processes, is significantly enhanced when LPS is added alone to the cultures. The LPS-induced nitrite increases are significantly reduced when cultures are pre-treated with either DMT, DET, DPT or 5-MeO-DMT. This desired effect is maintained in the presence of the 5-HT2A antagonist Ritanserin (Rit). Rat primary glial cultures were prepared from the cerebral cortex obtained from 2-day old animals. Cortical tissue was processed following previously published methods until high purity (>95%) separate cultures were obtained containing: a) microglial cells; b) astrocytes (detailed methods on cell type isolation and culture preparation are provided in the main text of current example 8). Individual cultures of each glial cell type were treated with: a) one of the four tryptamines at 1 μM in the absence of Rit, followed one hour later by LPS (10 μg/mL); or b) Rit at 1 μM for 1 h prior to tryptamine administration at 1 μM, followed 1 h later by LPS at 10 μg/mL. Exposure to LPS lasted 24 h, after which nitrite concentrations were determined. Vehicle-treated cultures were used as controls. Nitrite quantification: Culture supernatants were collected and assessed using the Griess reaction, which involves treatment with a specific reagent, incubation and finally measuring light absorbance within a specified wavelength range (a detailed description of the Griess procedure is provided in the main text of current example 8). All results are shown as bar graphs. Each bar represents the mean±SEM of 6 replications in 3 different experiments. ***p<0.001 indicates significant differences with cultures treated with LPS alone cells. A) Bar graphs showing results for DMT. As depicted in graphs A.1. and A.2., LPS administered alone induced a marked increase in nitrite levels in both microglia and astrocyte cultures, as compared to vehicle treated controls. DMT pre-treatment significantly reduced the nitrite increases, as compared to cultures treated with LPS alone. The DMT-induced reduction was maintained in the presence of the selective 5-HT2A receptor antagonist (Rit) for both microglial cells and astrocytes. B) Bar graphs showing results for DET, DPT and 5-MeO-DMT. Graphs B.1. and B.2. show a pattern of results analogous to those obtained for DMT. LPS-induced nitrite increases in both microglia and astrocyte cultures were significantly reduced by all three tryptamines. This effect was maintained in all cases in the presence of Rit. In all experiments, no statistically significant differences in nitrite levels were found between cultures treated with each tryptamine alone and those treated with the respective tryptamine in the presence of Rit. These results illustrate: a) The novel and unexpected finding that DMT, DET, DPT and 5-MeO-DMT display antiinflammatory effects on glial cells at the same concentration at which they promote neurogenesis. b) The innovative finding that the observed antiinflammatory effects are preserved in the presence of a 5-HT2A antagonist. Since 5-HT2A antagonists block the side effects of hallucinogenic tryptamines in humans, the proposed drug combination would retain the desired antiinflammatory effects on glial cells, while eliminating the undesired hallucinogenic effects.

Figure 9:
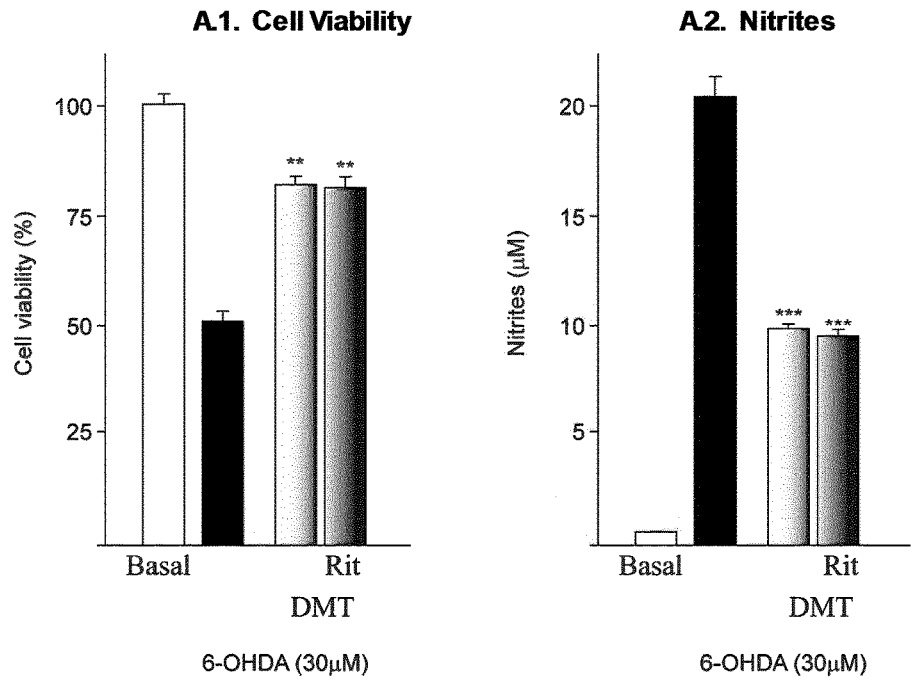
Figure 9:
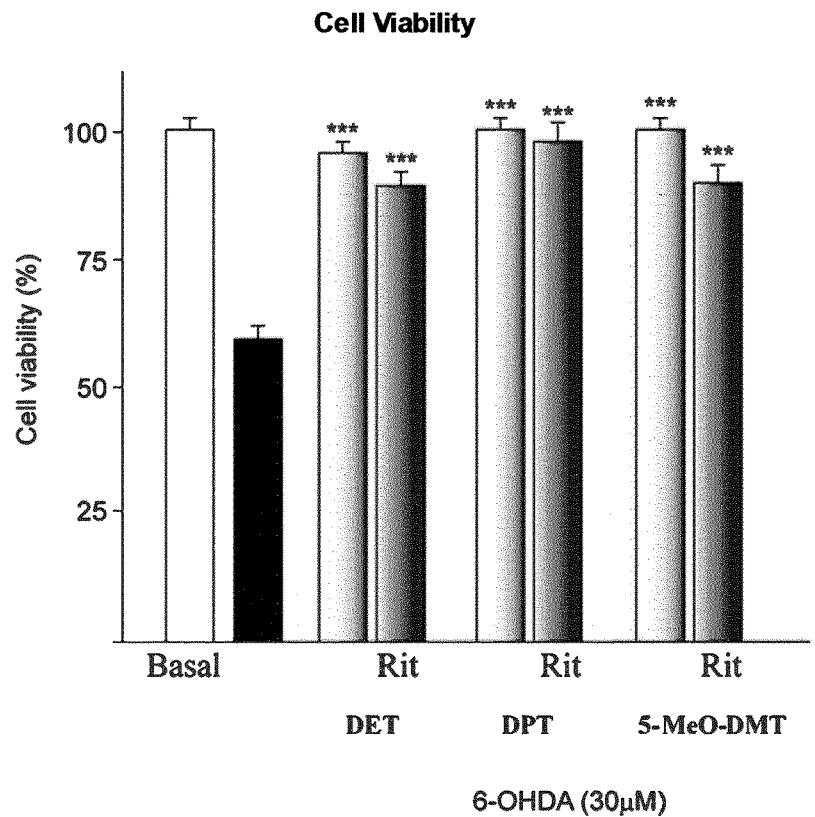

FIG. 9 DMT, DET, DPT and 5-MeO-DMT prevent dopaminergic cell death and inflammation in an in vitro model of Parkinson's Disease. Pre-treatment with each of the four tryptamines tested prevents cell death, and inflammation (only measured for DMT) caused by the administration of the neurotoxic compound 6-hydroxy-dopamine (6-OHDA) to cultured dopaminergic neurons. These beneficial effects were obtained using the same tryptamine concentration (1 μM) found to promote adult neurogenesis and to prevent glial inflammation (see FIGS. 1 to 4 and FIGS. 7 and 8). All four tryptamines reduce the dopaminergic cell death and enhanced nitrite production caused by 6-OHDA. These desired effects are preserved in the presence of the 5-HT2A antagonist Ritanserin (Rit). Human SH-SY5Y dopaminergic cells were cultured in 96-well plates and treated with either: a) one of the four tryptamines at 1 μM for 1 h, followed by 6-OHDA at 30 μM for 24 hours; or b) Rit at 1 μM for 1 h, followed by the tryptamine at 1 μM for an additional 1 h, at which point 6-OHDA was administered, also at 30 μM for 24 hours. Vehicle-treated cultures were used as controls. Twenty-four hours after 6-OHDA administration, cultures were assessed for cell viability and nitrite levels. Cell viability: quantification of viable dopaminergic cells after each treatment was conducted using the standard MTT assay. A detailed description of the procedure is provided in the main text of example 9. Nitrite quantification: Nitrite levels were assessed as indicators of an active inflammatory process. These measurements were only conducted in the experiments involving DMT alone and the DMT+Rit combination. Culture supernatants were collected at 24 h post-treatment and assessed using the Griess reaction method mentioned in FIG. 8 and described in detail in the text of Example 8, found in the "Examples" section of the application. All results are shown as bar graphs. Each bar represents the mean±SEM of 6 replications in 3 different experiments. *p<0.001; p<0.01 indicate significant differences with cultures treated with 6-OHDA alone. A) Bar graphs showing results obtained by using DMT. As depicted in graph A.1., 6-OHDA administered alone led to massive cell death, with a 50% reduction in the number of viable dopaminergic cells compared to vehicle treated cultures. Additionally, as depicted in graph A.2, exposure to the toxin caused a marked increase in nitrite concentrations. B) Bar graphs showing results for DET, DPT and 5-MeO-DMT. Here 6-OHDA alone also led to massive cell death, reducing cell viability to around 60% of the reference control value. Overall results show that culture pre-treatment with each of the four tryptamines tested in this example significantly reduced dopaminergic cell death, as indicated by the enhanced viability rates obtained. In the DMT experiments, where nitrite levels were also measured, the drug significantly reduced the nitrite levels in comparison to the levels observed after 6-OHDA alone. The neuroprotective activity demonstrated by all four tryptamines were preserved in the presence of a selective 5-HT2A receptor antagonist (Rit). No statistically significant differences were found when values of the assessed parameters were compared between cultures treated with each tryptamine alone and cultures treated with the same tryptamine in the presence of Rit. These results illustrate: a) The novel and unexpected finding that the hallucinogenic tryptamines DMT, DET, DPT and 5-MeO-DMT prevent dopaminergic cell death and the associated inflammatory process (assessment of inflammation could only be conducted for DMT) in an in vitro model of Parkinson's Disease that makes use of 6-OHDA, a potent neurotoxic agent that selectively targets dopaminergic neurons; b) The novel and unexpected finding that all four tryptamines tested prevented dopaminergic cell death at the same concentration at which they promote neurogenesis. c) The innovative finding that the protection against dopaminergic cell death brought about by hallucinogenic tryptamines is preserved in the presence of a 5-HT2A antagonist. Since 5-HT2A antagonists block the side effects of hallucinogenic tryptamines in humans, the proposed drug combination would retain the desired neuroprotective effects of dopaminergic neurons, while eliminating the undesired hallucinogenic effects.

Figure 10:
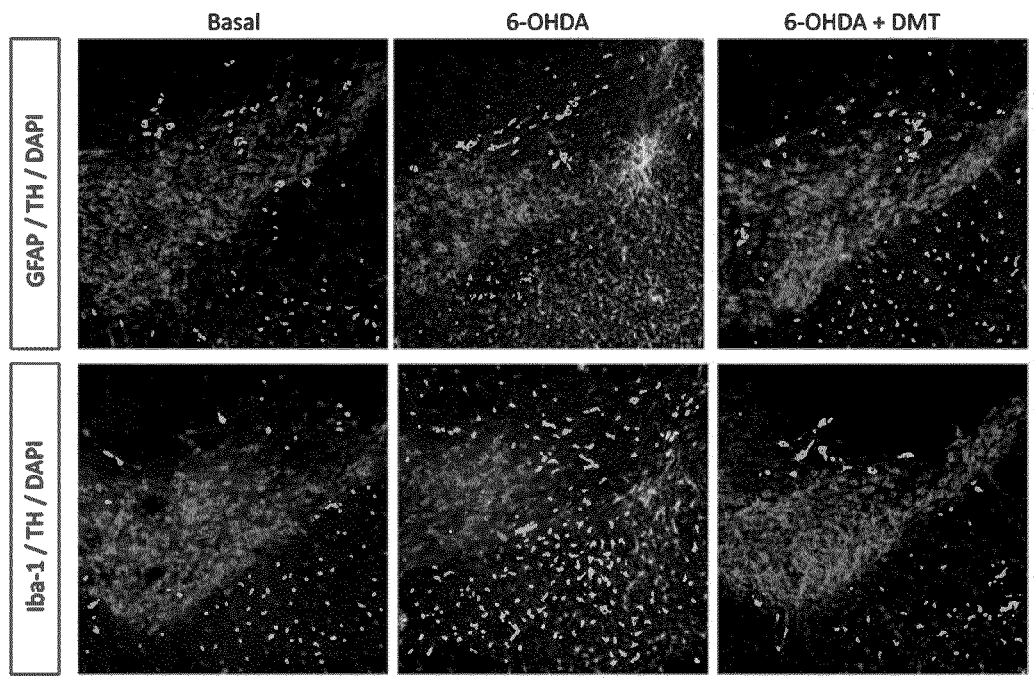
Figure 10:
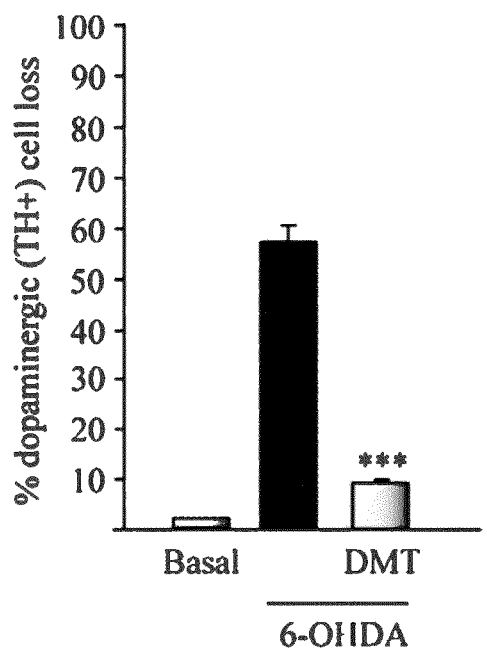

FIG. 10 DMT administration prevents dopaminergic cell death in an in vivo model of Parkinson's Disease. Adult mice were administered either: a) 5 µg of 6-hydroxydopamine (6-OHDA) or b) a combination of 5 µg 6-OHDA and 0.1 µg DMT. In both groups drugs were injected unilaterally into the Substantia nigra pars compacta. In each treatment arm, additional animals received a vehicle injection into the same brain area to serve as controls. Twenty one days after injection, animals treated with 6-OHDA alone showed signs of substantial dopaminergic cell death and microglial and astroglial activation, which are indicative of an inflammatory response. These effects were practically absent in the subgroup that received the combination of DMT and 6-OHDA. Adult mice were anesthetized and received single injections of the test drugs or vehicle in the right side of the Substantia nigra pars compacta (SNpc) using a stereotaxic apparatus. One group of animals was administered 5 µg of 6-OHDA. A second group was administered, also in a single injection, a combination consisting of 5 µg of 6-OHDA.plus 0.1 µg of DMT. A subgroup of animals in each treatment arm received, using the same methodology, injections containing only vehicle. After three weeks, brains were removed and tissue sections were processed for assessment. A) Representative images showing dopaminergic neurons labeled using tyrosine hydroxylase (TH) immunoreactivity, which in the original color image appears in red, and in the black and white images provided herein appear as dull white spots. Basal images can be used as reference with regard to the tone of white, given that the vast majority of cells in the image are dopaminergic cells. A GFAP marker was used to stain astroglial cells (upper row); and Iba-1 to label microglial cells (lower row). Both markers appear in green in color images. In the black and white images provided herein, they appear as brighter white spots. For comparison please note the practical absence of bright white spots in the basal images from vehicle treated animals. The images from 6-OHDA-treated animals clearly show a decrease in the number of dopaminergic neurons and an increase in activated astroglial and microglial cells. These effects are absent in the images from animals treated with the 6-OHDA+DMT combination. B) The number of dopaminergic (TH-immunoreactive cells) was quantified for each treatment group. Bars indicate the mean percentage cell loss relative to cell vehicle-treated animals. Each treatment condition (vehicle, 6-OHDA alone, and 6-OHDA+DMT) involved three separate experiments. Each experiment was carried out on four different animals. ***$p<0.001$ indicates the results of the statistical comparison with animals treated with 6-OHDA alone. As reflected in the figure, DMT co-administration markedly reduced dopaminergic cell loss, from a 60% average to a 10% average. These results illustrate: a) The novel and unexpected finding that the hallucinogenic tryptamine DMT prevents dopaminergic cell death and the associated inflammatory response in an in vivo model of Parkinson's Disease. b) The novel and unexpected finding that the in vivo effects of DMT appear to be of greater magnitude than those observed in our previous study, where DMT was tested in an in vitro model of Parkinson's Disease, as shown in FIG. 9.

SUMMARY OF THE INVENTION

The present application provides a pharmaceutical combination product, its use as a medicament, and its use as a medicament for the treatment and/or prevention of psychiatric and/or neurological disorders. The combination product comprises (i) a compound which promotes neurogenesis but has hallucinogenic or psychedelic side effects, and (ii) a 5-HT2A receptor antagonist which prevents, alleviates and/or removes the hallucinogenic or psychedelic side effects caused by the first compound. The compound and the 5-HT2A receptor antagonist can be administered together or separately. The neurogenic compound can be administered to an individual who is already taking a 5-HT2A receptor antagonist, and the 5-HT2A receptor antagonist can be administered to an individual who is already taking the neurogenic compound. Moreover, the combination product can be part of a kit for the treatment and/or prevention of psychiatric and/or neurological disorder.

DETAILED DESCRIPTION OF THE INVENTION

Definitions

The terms "treatment" and "therapy", as used in the present application, refer to a set of hygienic, pharmacological, surgical and/or physical means used with the intent to cure and/or alleviate a disease and/or symptoms with the goal of remediating the health problem. The terms "treatment" and "therapy" include preventive and curative methods, since both are directed to the maintenance and/or reestablishment of the health of an individual or animal. Regardless of the origin of the symptoms, disease and disability, the administration of a suitable medicament to alleviate and/or cure a health problem should be interpreted as a form of treatment or therapy within the context of this application.

The term "prevention", as used in the present application, refers to a set of hygienic, pharmacological, surgical and/or physical means used to prevent the onset and/or development of a disease and/or symptoms. The term "prevention" encompasses prophylactic methods, since these are used to maintain the health of an animal or individual.

The terms "individual", "patient" or "subject" are used interchangeably in the present application and are not meant to be limiting in any way. The "individual", "patient" or "subject" can be of any age, sex and physical condition. The term "animal", as used in the present application, refers to any multicellular eukaryotic heterotroph which is not a human. The term "therapeutically effective amount" refers to an amount of compound in a combination product which has a therapeutic effect and which is able to alleviate and/or cure a psychiatric and/or neurological disorder.

The term "psychiatric disorder" refers to a diagnosis by a mental health professional of a behavioral or mental pattern that may cause suffering or a poor ability to function in life. "Psychiatric disorders" may be persistent, relapsing and remitting, or occur as a single episode. In a preferred embodiment, the term "psychiatric disorder" refers to one or more disorders selected from the following: alcohol and substance use disorders, anxiety disorders, panic disorder, agoraphobia and other specific phobias, social anxiety disorder, post-traumatic stress disorder, obsessive compulsive disorder, generalized anxiety disorder, bipolar disorder, sleep and wake disorders, depression, anorexia nervosa, binge eating disorder, bulimia nervosa, psychosis, schizophrenia, autism spectrum disorders, developmental disorders, and personality disorders.

The term "neurological disorder" refers to any structural, biochemical and/or electrical abnormalities in the brain, spinal cord or other nerves. In a preferred embodiment, the term "neurological disorder" refers to one or more disorders selected from the following: acquired brain injury, ataxia, brain tumor, dementia, dystonia, epilepsy, temporal lobe epilepsy, pain associated with neurological disorders, headache disorders, functional and dissociative neurological symptoms, neuroinfections, meningitis, disorders associated with malnutrition, motor neuron disease, multi-system atrophy, multiple sclerosis, amyotrophic lateral sclerosis, mesial temporal lobe sclerosis, muscular dystrophy, myalgic encephalomyelitis, Parkinson's disease, progressive supranuclear palsy, cerebral palsy, Huntington's disease, Alzheimer's disease, fronto-temporal dementia, vascular dementia, dementia with Lewy bodies, corticobasal degeneration, Lyme encephalopathy, toxic encephalopathy, cognitive decline associated with aging, spina bifida, hydrocephalus, spinal injury, stroke, Tourette syndrome, and transverse myelitis.

The term "side effect", as used in the present application, refers to unwanted and/or unintended secondary effects caused by the administration of a medicament to an individual. The terms "hallucinogenic side effects" and "psychedelic side effects" are used in the present application interchangeably to refer to unwanted and/or unintended secondary effects caused by the administration of a medicament to an individual resulting in subjective experiences being qualitatively different from those of ordinary consciousness. These experiences can include derealization, depersonalization, hallucinations and/or sensory distortions in the visual, auditory, olfactory, tactile, proprioceptive and/or interoceptive spheres and/or any other perceptual modifications, and/or any other substantial subjective changes in cognition, memory, emotion and consciousness.

The term "receptor" refers to a protein molecule present on the membrane or in the interior of the cell that receives chemical signals (i.e., interacts with endogenous and/or exogenous molecules), leading to: a) the blockade of the said protein molecule (e.g. as caused by receptor antagonists); or b) a cellular response upon binding to the chemical signals (e.g. as caused by receptor agonists, partial agonists, inverse agonists and allosteric modulators).

The 5-hydroxytryptamine receptor 2A (5-HT2A) is a subtype of the 5-HT receptors that belongs to the serotonin receptor family and is a G protein-coupled receptor. The 5-HT2A receptor is found in humans and the receptor has been sequenced, characterized and the data have been deposited in the UniProtKB database under the accession number P28223.

The 5-hydroxytryptamine receptor 1A (5-HT1A) is a subtype of the 5-HT receptors that belongs to the serotonin receptor family and is a G protein-coupled receptor. The 5-HT1A receptor is found in humans and the receptor has been sequenced, characterized and the data have been deposited in the UniProtKB database under the accession number P08908.

The Sigma-1 receptor is a chaperone protein at the endoplasmic reticulum that modulates calcium signaling. The Sigma-1 receptor is found in humans and the receptor has been sequenced, characterized and the data have been deposited in the UniProtKB database under the accession number Q99720.

The term "receptor antagonist" as used in the present application refers to a type of receptor ligand and/or drug that blocks or dampens agonist- or partial agonist-mediated responses rather than provoking a biological response itself upon binding to a receptor. The term "receptor agonist" refers to a type of receptor ligand and/or drug that activates the receptor to produce a full (full agonist) or partial (partial agonist) biological response. As used in the present application, the term "receptor antagonist" may also refer to a type of receptor ligand and/or drug that activates the receptor to produce a biological response that is opposed to that produced by a full or partial agonist. Although these compounds are technically known as "inverse agonists", here we use the term "receptor antagonist" to encompass both antagonists and inverse agonists. The reason being that some reports in the scientific literature initially labeled a given compound as an "antagonist", while subsequent more detailed studies have found the same compound to display inverse agonist activity. Both antagonists and inverse agonists effectively counteract the effects of agonists (full or partial). The term "monoamine oxidase" refers to a family of enzymes that catalyze the oxidation of monoamines. The EC number of this class of enzyme is 1.4.3.4. In humans, there are two types of monoamine oxidases (MAOs): MAO-A and MAO-B. Data concerning MAO-A have been deposited in the UniProtKB database under the accession number P21397 and data concerning MAO-B have been deposited under the accession number P27338.

The term "proliferation", as used in the present application, refers to the growth of cell populations wherein the cells grow and divide.

The term "differentiation", as used in the present application, refers to the process where a progenitor cell gives rise to a specific cell phenotype. For example, neural stem cells can primarily, without limiting the scope of the invention, differentiate into neurons, astrocytes and oligodendrocytes.

The term "neural stem cell", refers to self-renewing, multipotent cells that generate the different type of cells of the Nervous System (e.g. neurons and glial cells).

The term "combination product" can refer to (i) a product comprised of two or more regulated components that are physically, chemically, or otherwise combined or mixed and produced as a single entity; (ii) two or more separate products packaged together in a single package or as a unit and comprised of drug and device products, device and biological products, or biological and drug products; (iii) a drug, device, or biological product packaged separately that according to its investigational plan or proposed labeling is intended for use only with an approved individually specified drug, device, or biological product where both are required to achieve the intended use, indication, or effect and where upon approval of the proposed product the labeling of the approved product would need to be changed, e.g., to reflect a change in intended use, dosage form, strength, route of administration, or significant change in dose; or (iv) any investigational drug, device, or biological product packaged separately that according to its proposed labeling is for use only with another individually specified investigational drug, device, or biological product where both are required to achieve the intended use, indication, or effect.

As used herein, "pharmaceutically acceptable carrier" or "pharmaceutically acceptable diluent" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and, without limiting the scope of the present invention, include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone. Other pharmaceutically acceptable carriers, excipients, or stabilizers, such as those described in Remington's Pharmaceutical Sciences 16th edition, Osol, A. Ed. (1980) may also be included.

The term "controlled substance" refers to any substantially pure molecule with a therapeutic effect which is well known and/or studied. An example of a controlled substance may be any active ingredient currently approved by the FDA or EMA.

The term "substantially pure" refers to any compound that has been separated from its surrounding environment and has been enriched in a sample. A compound is substantially pure if the compound made up at least 50, 55, 60, 70, 75, 85, 90 or 95% of a sample at any point. Preferably, the compound made up at least 95% of a sample at any point. The compound is substantially pure before it is mixed with other components such as another active ingredient or pharmaceutically acceptable carriers and/or diluents. Further, when the purity is measured in solution, the one or more solvents used are not included in the calculation of the purity of the compound in the sample. The purity may be measured through any common method known in the art. For example, the purity of the compound in the sample may be determined through high-performance liquid chromatography (HPLC).

In a preferred embodiment, the purity of a substantially pure compound in a sample is determined through HPLC.

The term "active ingredient", as used herein, refers to the component of a pharmaceutical combination product or pharmaceutical composition which is biologically active. In the present application, an active ingredient may comprise one or more compounds. The term does not encompass inactive ingredients such as pharmaceutically active carriers and/or diluents.

For the avoidance of any doubt, the terms "pharmaceutical combination product" and "combination product" are used interchangeably throughout the present disclosure. Both refer to a combination product for pharmaceutical use.

Combination Product

In a first aspect, the present application provides a pharmaceutical combination product. The combination product comprises (i) a compound which promotes neurogenesis and has hallucinogenic or psychedelic side effects, and (ii) a 5-HT2A receptor antagonist which prevents, alleviates and/or removes the hallucinogenic or psychedelic side effects caused by the first compound.

In a preferred embodiment, the combination product is a combination product which comprises (i) a compound described by the following formula (I):

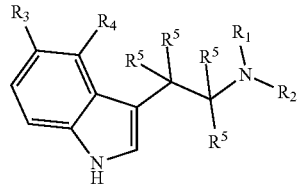

Formula (I)

wherein R1 is selected from the group consisting of methyl, ethyl, n-propyl, allyl and isopropyl;
wherein R2 is selected from the group consisting of methyl, ethyl, n-propyl, allyl and isopropyl;
wherein R3 is selected from the group consisting of hydrogen, methoxy, methyl, hydroxy and a halogen (preferably the halogen is fluorine, chlorine or bromine); and
wherein R4 is selected from the group consisting of hydrogen, hydroxy, phosphoryloxy and acetoxy;
wherein R5 is selected from the group consisting of deuterium ($^2$H) and protium ($^1$H); and (ii) a 5-HT2A receptor antagonist.

Rather than a complex mixture of natural compounds derived from vegetation, the two active ingredients of the present invention may be substantially pure and may or may not be combined with pharmaceutically acceptable carrier and/or diluent as well as other controlled substances. In a preferred embodiment, the compound described by formula (I) is substantially pure.

In a preferred embodiment, the active ingredient present in the combination product consists of a compound described by formula (I), a 5-HT2A receptor antagonist and, optionally, a monoamine oxidase inhibitor. In other words, in a preferred embodiment, the only active ingredients present in the pharmaceutical combination product are a compound described by formula (I), a 5-HT2A receptor antagonist and, optionally, a monoamine oxidase inhibitor.

Preferably, the compound described by formula (I) is N,N-dimethyltryptamine, N,N-diethyltryptamine, N,N-dipropyltryptamine, N,N-diisopropyltryptamine, 5-methoxy-N,N-dimethyltryptamine, 5-methoxy-N,N-diisopropyltryptamine, 5-hydroxy-N,N-dimethyltryptamine (bufotenin), 4-phosphoryloxy-N,N-dimethyltryptamine (psilocybin), 4-hydroxy-N,N-dimethyltryptamine (psilocin), N,N-diallyltryptamine, 5-Fluoro-N,N-diallyltryptamine, 5-Chloro-N,N-diallyltryptamine, 5-Bromo-N,N-diallyltryptamine, 5-Methyl-N,N-diallyltryptamine, 5-Methoxy-N,N-diallyltryptamine, $\alpha,\alpha,\beta,\beta$,-tetradeutero-5-Methoxy-dimethyltryptamine, $\alpha,\alpha,\beta,\beta$,-tetradeutero-dimethyltryptamine and/or O-acetylpsilocin. More preferably, the compound described by formula (I) is N,N-dimethyltryptamine, N,N-diethyltryptamine, N,N-dipropyltryptamine and/or N,N-diisopropyltryptamine; or the compound described by formula (I) is N,N-dimethyltryptamine, N,N-diethyltryptamine, N,N-dipropyltryptamine, N,N-diisopropyltryptamine and/or 5-methoxy-N,N-dimethyltryptamine. Most preferably, the compound described by formula (I) is N,N-dimethyltryptamine.

In a preferred embodiment, the compound described by formula (I) is administered as a free base, salt, ester, prodrug or dimer linked to a suitable chemical moiety which is or can then be converted into the compound described by formula (I) in the body of the patient.

N,N-dimethyltryptamine (CAS No. 61-50-7) can be purchased from Sigma-Aldrich (Cat. No. SML0791), extracted from N,N-dimethyltryptamine-containing plants such as *Psychotria viridis* or chemically synthesized (Brandt et al., 2010. *Drug Test Anal.* 2 (7): 330-8). N,N-diethyltryptamine (CAS No. 61-51-8), N,N-dipropyltryptamine (CAS No. 61-52-9), N,N-diisopropyltryptamine (PubChem ID 26903), and 5-methoxy-N,N-dimethyltryptamine (PubChem ID 1832), can be chemically synthesized (Valter and Arrizabalaga, 1998. *Designer Drugs Directory*). 5-methoxy-N,N-diisopropyltryptamine (PubChem ID 151182) can be chemically synthesized (Xu and Chen, 2006. *J. Label Compd Radiopharm.* 49 (10): 897-902). Bufotenin (PubChem ID 10257) can be extracted from the venom of toads such as toads belonging to the species *Bufo alvarius* and bufotenin can be chemically synthesized (Somei et al., 2001. *Chem Pharm Bull* (Tokyo). Psilocybin (PubChem ID 10624) and psilocin (PubChem ID 4980) can be extracted from mushrooms, chemically synthesized (Hofmann et al., 1959. *Helvetica Chimica Acta.* 42 (5): 1557-72) or purchased from Sigma-Aldrich (Cat. No. P-097 and P2279). O-acetylpsilocin (PubChem ID 15429212) can be synthesized as described in U.S. Pat. No. 3,075,992.

N,N-diallyltryptamine, 5-Fluoro-N,N-diallyltryptamine, 5-Chloro-N,N-diallyltryptamine, 5-Bromo-N,N-diallyltryptamine, 5-Methyl-N,N-diallyltryptamine and 5-Methoxy-N,N-diallyltryptamine have been synthesized previously (Cozzi and Daley, 2016. *Bioorg Med Chem Lett.* 26(3):959-964). $\alpha,\alpha,\beta,\beta$,-tetradeutero-5-Methoxy-dimethyltryptamine and $\alpha,\alpha,\beta,\beta$,-tetradeutero-dimethyltryptamine have also been synthesized previously (Halberstadt et al., 2012. *Psychopharmacology.* 221(4):709-18; Beaton et al., 1982. *Pharmacol Biochem Behav.* 16(5):811-4).

Preferably, the 5-HT2A receptor antagonist is: Methiothepin (CAS No. 20229-30-5), Ketanserin (CAS No. 74050-98-9), Flibanserin (CAS No. 167933-07-5), Methysergide (CAS No. 361-37-5), Trazodone (CAS No. 19794-93-5), Nefazodone (CAS No. 83366-66-9), Cinitapride (CAS No. 66564-14-5), Cyproheptadine (CAS No. 129-03-3), Brexpiprazole (CAS No. 913611-97-9), Cariprazine (CAS No. 839712-12-8), Agomelatine (CAS No. 138112-76-2), Pimavanserin (CAS No. 706779-91-1), Eplivanserin (CAS No. 130579-75-8), Volinanserin (CAS No. 139290-65-6), Altanserin (CAS No. 76330-71-7), Setoperone (CAS No. 86487-64-1), Ritanserin (CAS No. 87051-43-2), LY-367,265 (CAS No. 210751-39-6), 1-(1-Naphthyl)piperazine (CAS No. 57536-86-4 J19924), SB 206553 (CAS No. 158942-04-2), Pirenperone (CAS No. 75444-65-4), SB-215505 (CAS No. 162100-15-4), Metergoline (CAS No. 17692-51-2), Deramciclane (CAS No. 120444-71-5), Amperozide (CAS No. 75558-90-6), Glemanserin (CAS No. 132553-86-7), 5-MeO-NBpBrT (CAS No. 155639-13-7), Adatanserin (CAS No. 127266-56-2), AMDA (CAS No. 22136-76-1), Cinanserin (CAS No. 1166-34-3), Fananserin (CAS No. 127625-29-0), Iferanserin (CAS No. 58754-46-4), AC-90179 (CAS No. 359878-17-4), LY86057 (CAS No. 148966-66-9), GSK-215083 (CAS No. 887923-36-6), Cyamemazine (CAS No. 3546-03-0), Mesulergine (CAS No. 64795-35-3), BF-1 (CAS No. 518980-66-0), LY215840 (CAS No. 137328-52-0), Sergolexole (CAS No. 108674-86-8), Spiramide (CAS No. 510-74-7), LY53857 (CAS No. 60634-51-7), Amesergide (CAS No. 121588-75-8), LY108742 (CAS No. 150196-69-3), Pipamperone (CAS No. 1893-33-0), LY314228 (CAS No. 182633-54-1) and/or 5-I-R91150 (CAS No. 155928-24-8). More preferably, the 5-HT2A receptor antagonist is methiothepin, ritanserin and/or ketanserin.

Details of the 5-HT2A antagonists are provided below:

Methiothepin
Activity: Antagonist/Inverse agonist at 5-HT2A/1A with similar affinity.
Vendor: Sigma-Aldrich as mesylate salt
Vendor Catalog No.: 149

Ketanserin
Activity: 5-HT2A Antagonist/Inverse Agonist
Vendor: Sigma-Aldrich as tartrate salt
Vendor Catalog No.: S006

Flibanserin
Activity: 5-HT2A Antagonist/5-HT1A Agonist/D4 Antagonist
Vendor: Sigma-Aldrich
Vendor Catalog No.: ZML0797

Methysergide
Activity: 5-HT2A/2C receptor Antagonist, 5-HT2B partial agonist, 5-HT1A Agonist
Vendor: Sigma-Aldrich as maleate salt
Vendor Catalog No.: M137

Trazodone
Activity: 5-HT2A/2C antagonist, 5-HT1A partial agonist, H1 Antagonist
Vendor: Sigma-Aldrich as hydrochloride salt
Vendor Catalog No.: T6154

Nefazodone
Activity: 5-HT2A/1A receptor Antagonist
Vendor: Sigma-Aldrich as hydrochloride salt
Vendor Catalog No.: 363464

Cinitapride
Activity: 5HT2A Antagonist, 5HT4 Agonist, 5HT1A Agonist
Vendor: AKos Consulting & Solutions
Vendor Catalog No.: AKOS015909742

Cyproheptadine
Activity: 5-HT2A/2C receptor Antagonist. Anti H1 and Anti-muscarinic activity
Vendor: Sigma Aldrich
Vendor Catalog No.: C3280000 as hydrochloride salt Brexpiprazole
Activity: 5-HT2A Antag, 5-HT1A agonist/partial agonist, D2 agonist/partial agonist
Vendor: Sigma-Aldrich
Vendor Catalog No.: ADV465748754

Cariprazine
Activity: 5-HT2A Antagonist, 5-HT1A agonist/partial agonist, D2, D3 agonist/partial agonist
Vendor: Sigma-Aldrich
Vendor Catalog No.: ADV 638391880
Agomelatine
Activity: Melatonin MT1 & MT1 Agonist//5-HT2A/2C receptor Antagonist
Vendor: Axon MedChem BV
Vendor Catalog No.: 1492
Pimavanserin
Activity: 5-HT2A Inverse Agonist
Vendor: Boc Sciences
Vendor Catalog No.: 706779-91-1
Eplivanserin
Activity: 5-HT2A receptor Antagonist
Vendor: Sigma Aldrich
Vendor Catalog No.: S7201 as hemifumarate salt
Volinanserin
Activity: 5-HT2A receptor Antagonist
Vendor: Sigma-Aldrich
Vendor Catalog No.: M3324
Altanserin
Activity: 5-HT2A Antagonist
Vendor: Sigma Aldrich
Vendor Catalog No.: A8106 as hydrochloride salt
Setoperone
Activity: 5-HT2A Antagonist
Vendor: ZINC
Vendor Catalog No. ZINC538339
Ritanserin
Activity: Antag 5-HT2A/2B/2C and much lower at 5-HT1A
Vendor: Sigma-Aldrich
Vendor Catalog No. R103
LY-367,265
Activity: Antagonist 5-HT2A, Serotonin reuptake inhibitor
Vendor: Sigma-Aldrich
Vendor Catalog No. L2411_SIGMA
1-(1-Naphthyl)piperazine
Activity: Antagonist 5-HT2A/Agonist 5-HT1A
Vendor: Manchester Organics
Vendor Catalog No. J19924J19924
SB 206553
Activity: Antag 5-HT2A/2B/2C
Vendor: Sigma-Aldrich
Vendor Catalog No. S180
Pirenperone
Activity: 5-HT2A receptor Antagonist
Vendor: Santa Cruz Biotechnology
Vendor Catalog No. sc-253280
SB-215505
Activity: Selective 5-HT2B antagonist, less so 5-HT2A/C
Vendor: Sigma Aldrich
Vendor Catalog No. S1068
Metergoline
Activity: Antagonist at 5-HT2A/2B/2C and multiple other 5-HT receptor subtypes
Vendor: Sigma Aldrich
Vendor Catalog No.: M3668
Deramciclane
Activity: 5-HT2A Antagonist/5-HT2C Inverse Agonist
Vendor: BOC Sciences.
Vendor Catalog No.: 120444-71-5
Amperozide
Activity: 5HT2A Antagonist (Ki 12 nM), D2 Antag (Ki 140 nM)
Vendor: AKos Consulting & Solutions
Vendor Catalog No.: AKOS030548015
Glemanserin
Activity: 5-HT2A receptor Antagonist
Vendor: Biosynth
Vendor Catalog No.: J-002002
5-MeO-NBpBrT
Activity: 5-HT2A receptor Antagonist
Vendor: Chembase
Vendor Catalog No.: 125495
Adatanserin
Activity: 5-HT2A receptor Antagonist
Vendor: ZINC
Vendor Catalog No.: ZINC53046001
AMDA
Activity: 5-HT2A receptor Antagonist
Vendor: ZINC
Vendor Catalog No.: ZINC 13473096
Cinanserin
Activity: 5-HT2A/2C receptor Antagonist
Vendor: Biosynth
Vendor Catalog No.: J-003464
Fananserin
Activity: 5-HT2A receptor Antagonist, D4 receptor Antagonist
Vendor: Biosynth
Vendor Catalog No.: J-005514
Iferanserin
Activity: 5-HT2A receptor Antagonist
Vendor: Zinc
Vendor Catalog No. ZINC5599842
AC-90179
Activity: 5-HT2A Antagonist. Lower affinity 5-HT2C Antagonist
Vendor: Med Koo Biosciences, Inc.
Vendor Catalog No.: 531399
LY86057
Activity: 5-HT2A/2B Antagonist with similar affinity
Vendor: Med Koo Biosciences, Inc.
Vendor Catalog No.: 532173
GSK-215083
Activity: 5-HT2A/5-HT6 receptor Antagonist
Vendor: Med Koo Biosciences, Inc.
Vendor Catalog No.: 525210
Cyamemazine
Activity: 5-HT2A/2C Antagonist, Lower Affinity 5-HT1A Antagonist
Vendor: Boc Sciences
Vendor Catalog No.: BOC13751
Mesulergine
Activity: 5-HT2A antagonist/5-HT2A Inverse Agonist
Vendor: Santa Cruz Biotechnology
Vendor Catalog No.: sc-361251, hydrochloride salt
BF-1
Activity: 5-HT2A/2B receptor Antagonist
Vendor: ChemTik
Vendor Catalog No.: CTK1E4820
LY215840
Activity: 5-HT2A receptor Antagonist
Vendor: Santa Cruz Biotechnology
Vendor Catalog No.: sc-361236

Sergolexole
Activity: 5-HT2A receptor Antagonist
Vendor: Leancare Ltd.
Vendor Catalog No.: BRS0000746
Spiramide
Activity: 5-HT2A receptor Antagonist. Lower affinity 5-HT2B/2C Antagonist
Vendor: Alfa Chemistry
Vendor Catalog No.: ACM3824917
LY53857
Activity: 5-HT2A/2B Antagonist
Vendor: Med Koo Biosciences, Inc.
Vendor Catalog No.: 525549
Amesergide
Activity: 5-HT2A receptor Antagonist
Vendor: American Custom Chemicals Corporation
Vendor Catalog No.: BRS0000415
LY108742
Activity: 5-HT2A receptor Antagonist
Vendor: American Custom Chemicals Corporation
Vendor Catalog No.: BRS0000550
Pipamperone
Activity: 5-HT2A Antagonist/Lower affinity 5-HT1A Antagonist
Vendor: Boc Sciences
Vendor Catalog No.: BOC26805
LY314228
Activity: 5-HT2A receptor Antagonist
Vendor: Med Koo Biosciences, Inc.
Vendor Catalog No.: 532157
5-I-R91150
Activity: 5-HT2A receptor Antagonist
Vendor: Leancare Ltd.
Vendor Catalog No.: c211762157

In a preferred embodiment, the 5-HT2A receptor antagonist is not a 5-HT1A receptor antagonist. In a preferred embodiment, the 5-HT2A receptor antagonist selectively binds 5-HT2A. In a preferred embodiment, the 5-HT2A receptor antagonist is a mixed receptor antagonist which binds 5-HT2A and 5-HT1A but preferentially acts on the 5-HT2A receptor.

In a preferred embodiment, the combination product comprises (i) N,N-dimethyltryptamine, N,N-diethyltryptamine, N,N-dipropyltryptamine and/or N,N-diisopropyltryptamine, and (ii) methiothepin, ritanserin, and/or ketanserin. Most preferably, the combination product comprises (i) N,N-dimethyltryptamine and (ii) methiothepin.

In an alternative embodiment, the combination product comprises (i) N,N-dimethyltryptamine, N,N-diethyltryptamine, N,N-dipropyltryptamine and/or N,N-diisopropyltryptamine, and (ii) ketanserin.

In an alternative embodiment, the combination product comprises (i) N,N-dimethyltryptamine, N,N-diethyltryptamine, N,N-dipropyltryptamine and/or N,N-diisopropyltryptamine, and (ii) ritanserin.

In a preferred embodiment, the combination product comprises (i) N,N-dimethyltryptamine, N,N-diethyltryptamine, N,N-dipropyltryptamine, N,N-diisopropyltryptamine and/or 5-methoxy-N,N-dimethyltryptamine, and (ii) methiothepin, ritanserin, and/or ketanserin. Most preferably, the combination product comprises (i) N,N-dimethyltryptamine and (ii) methiothepin.

In an alternative embodiment, the combination product comprises (i) N,N-dimethyltryptamine, N,N-diethyltryptamine, N,N-dipropyltryptamine and/or 5-methoxy-N,N-dimethyltryptamine, and (ii) ketanserin.

In an alternative embodiment, the combination product comprises (i) N,N-dimethyltryptamine, N,N-diethyltryptamine, N,N-dipropyltryptamine and/or 5-methoxy-N,N-dimethyltryptamine, and (ii) ritanserin.

In a preferred embodiment, any of the aforementioned combination products may further comprise a monoamine oxidase inhibitor which can boost the effectiveness of the compound described by formula (I). Preferably, the monoamine oxidase inhibitor is: a) a β-carboline such as harmine (CAS No. 442-51-3), harmaline (CAS No. 304-21-2), tetrahydroharmine (CAS No. 17019-01-1), harmol (CAS No. 487-03-6), and/or harmalol (CAS No. 525-57-5), their salts and/or esters; and/or b) one or more of the following compounds: moclobemide (CAS No. 71320-77-9), pargyline (CAS No. 555-57-7), isocarboxazid (CAS No. 59-63-2), pirlindole (CAS No. 60762-57-4), toloxatone (CAS No. 29218-27-7), selegiline (CAS No. 14611-51-9), phenelzine (CAS No. 51-71-8), tranylcypromine (CAS No. 155-09-9), rasagiline (CAS No. 136236-51-6), phenmetrazine (CAS No. 1707-14-8), minaprine (CAS No. 25905-77-5), furazolidone (CAS No. 67-45-8), and procarbazine (CAS No. 671-16-9).

In a preferred embodiment, the combination product is a mixture of the compound described by formula (I) and the 5-HT2A receptor antagonist, i.e. the combination product is a composition. In an alternative embodiment, the compound described by formula (I) and the 5-HT2A receptor antagonist are physically separated. For example, the compound described by formula (I) could be contained in one blister pack while the 5-HT2A receptor antagonist is contained within a separate blister pack or the compound described by formula (I) and the 5-HT2A receptor antagonist could be contained in the same pill but be physically separated by a barrier, such as a gelatin barrier.

In a preferred embodiment, the combination product is contained within one or two tablets which further comprise common excipients and the tablet(s) is/are suitable for oral administration. The tablet(s) may comprise (i) a core comprising a therapeutically effective amount of a compound described by formula (I) and/or a 5-HT2A receptor antagonist, a first control-release coating comprising a water-insoluble water-permeable film-forming polymer, a plasticizer and a water-soluble polymer. The tablet(s) may further comprise a moisture barrier surrounding said first control-releasing coat, wherein the moisture barrier comprises an enteric polymer, a plasticizer and a permeation enhancer.

Non-limiting examples of water-insoluble water-permeable film-forming polymers useful for the control-releasing coat include cellulose ethers, cellulose esters, and polyvinyl alcohol. Non-limiting examples of plasticizers useful for the control-releasing coat described herein include polyols, such as polyethylene glycol of various molecular weights, organic esters, such as diethyl phthalate or triethyl citrate, and oils/glycerides such as fractionated coconut oil or castor oil. Non-limiting examples of water-soluble polymers useful for the control-releasing coat include polyvinylpyrrolidone, hydroxypropyl methylcellulose and hydroxypropyl cellulose. The preferred water-soluble polymer is polyvinylpyrrolidone. Non-limiting examples of enteric polymers useful for the moisture barrier include acrylic polymers such as a methacrylic acid copolymer type C [poly(methacrylic acid, methyl methacrylate) 1:1] available commercially under the trade name Eudragit® (e.g. Eudragit L 30 D-55). Non-limiting examples of permeation enhancers useful for the moisture barrier include silicon dioxide, colloidal silicon, lactose, hydrophilic polymers, sodium chloride, aluminum oxide, colloidal aluminum oxide, silica, microcrystalline cellulose and any combination thereof.

In a preferred embodiment, the aforementioned tablet(s) or any alternative tablet arrangement conceivable by a skilled person, e.g. such as a tablet formulation which keeps the compound described by formula (I) and the 5-HT2A receptor antagonist physically separated before administration, may be contained in one or more blister packs.

In a preferred embodiment, the combination product comprises a compound described by formula (I) and instructions on how to administer the compound described by formula (I) with a 5-HT2A receptor antagonist which may or may not be sold separately. In another preferred embodiment, the combination product comprises a 5-HT2A receptor antagonist and instructions on how to administer the 5-HT2A receptor antagonist with a compound described by formula (I) which may or may not be sold separately.

In a preferred embodiment, the combination product may comprise one or more solution(s) which are suitable for intravenous, intramuscular, transdermal and/or subcutaneous administration. In another embodiment, the combination product may comprise one or more solution(s) which are suitable for sublingual, buccal and/or inhalation-mediated administration routes. In an alternative embodiment, the combination product may comprise one or more aerosol(s) which are suitable for inhalation-mediated administration.

In a preferred embodiment, the combination product may comprise one or more cream(s) and/or ointment(s) which are suitable for topical administration. In a preferred embodiment, the combination product may comprise one or more suppositories which are suitable for rectal administration.

The combination product may comprise any combination of tablets, solutions, aerosols, creams, ointments and/or suppositories as long as the combination product stimulates the proliferation and/or differentiation of neural stem cells and causes less hallucinogenic and/or psychedelic side effects than a combination product which does not comprise a 5-HT2A receptor antagonist.

In a preferred embodiment, the combination product is administered at least two times, preferably more than two times. A dosage of the combination product can comprise 0.5-1000 mg of a compound described by formula (I) and/or 0.5-1000 mg of a 5-HT2A receptor antagonist.

In a preferred embodiment, the compound described by formula (I) exerts a neuroprotective and anti-inflammatory effect thereby preventing neural cell degeneration, neural cell death and/or inflammatory responses associated with neural cell degeneration and/or death.

Uses of the Combination Product

In a second aspect, the combination product of the present invention can be used as a medicament. In a third aspect, the combination product of the present invention can be used for the treatment and/or prevention of psychiatric and/or neurological disorders.

In a preferred embodiment, the psychiatric and/or neurological disorder is acquired brain injury, ataxia, brain tumor, dementia, dystonia, epilepsy, functional and dissociative neurological symptoms, meningitis, motor neuron disease, multiple sclerosis, muscular dystrophy, myalgic encephalomyelitis, Parkinson's disease, progressive supranuclear palsy, Huntington's disease, Alzheimer's disease, fronto-temporal dementia, spina bifida, hydrocephalus, spinal injury, stroke, Tourette syndrome, transverse myelitis, panic disorder, agoraphobia, social anxiety disorder, phobias, post-traumatic stress disorder, obsessive compulsive disorder, generalized anxiety disorder, bipolar disorder, depression, anorexia nervosa, binge eating disorder, bulimia nervosa, psychosis, schizophrenia, substance addiction and/or personality disorders. Preferably, the psychiatric and/or neurological disorder is depression, addiction, post-traumatic stress disorder, personality disorders, neurodegenerative and/or vascular dementias.

In a preferred embodiment, the combination product of the present invention can be used for the treatment and/or prevention of psychiatric disorders. Preferably, the psychiatric disorder is panic disorder, agoraphobia, social anxiety disorder, phobias, post-traumatic stress disorder, obsessive compulsive disorder, generalized anxiety disorder, bipolar disorder, depression, anorexia nervosa, binge eating disorder, bulimia nervosa, psychosis, schizophrenia, substance addiction and/or personality disorders. More preferably, the psychiatric disorders are depression, addiction, post-traumatic stress disorder and/or personality disorders.

In a preferred embodiment, the combination product of the present invention can be used for the treatment and/or prevention of neurological disorders. Preferably, the neurological disorder is acquired brain injury, ataxia, brain tumor, dementia, dystonia, epilepsy, functional and dissociative neurological symptoms, meningitis, motor neuron disease, multiple sclerosis, muscular dystrophy, myalgic encephalomyelitis, neurodegenerative diseases including Parkinson's disease, progressive supranuclear palsy, Huntington's disease, Alzheimer's disease, and fronto-temporal dementia; spina bifida, hydrocephalus, spinal injury, stroke, Tourette syndrome and/or transverse myelitis. More preferably, the neurological disorders are neurodegenerative and/or vascular dementias.

In a preferred embodiment, the combination product of the present invention can be used for the treatment and/or prevention Parkinson's Disease and/or Alzheimer's disease. Preferably, the combination product of the present invention can be used for the treatment and/or prevention Parkinson's Disease.

Kit

In a fourth aspect, the combination product of the present invention is part of a kit for the treatment and/or prevention of psychiatric and/or neurological disorders.

In a preferred embodiment, the psychiatric and/or neurological disorder is acquired brain injury, ataxia, brain tumor, dementia, dystonia, epilepsy, functional and dissociative neurological symptoms, meningitis, motor neuron disease, multiple sclerosis, muscular dystrophy, myalgic encephalomyelitis, Parkinson's disease, progressive supranuclear palsy, Huntington's disease, spina bifida, hydrocephalus, spinal injury, stroke, Tourette syndrome, transverse myelitis, panic disorder, agoraphobia, social anxiety disorder, phobias, post-traumatic stress disorder, obsessive compulsive disorder, generalized anxiety disorder, bipolar disorder, depression, anorexia nervosa, binge eating disorder, bulimia nervosa, psychosis, schizophrenia, substance addiction and/ or personality disorders. Preferably, the psychiatric and/or neurological disorders are depression, addiction, post-traumatic stress disorder, personality disorders, neurodegenerative and/or vascular dementias.

In a preferred embodiment, the kit of the present invention can be used for the treatment and/or prevention of psychiatric disorders. Preferably, the psychiatric disorder is panic disorder, agoraphobia, social anxiety disorder, phobias, post-traumatic stress disorder, obsessive compulsive disorder, generalized anxiety disorder, bipolar disorder, depression, anorexia nervosa, binge eating disorder, bulimia nervosa, psychosis, schizophrenia, substance addiction and/or personality disorders. More preferably, the psychiatric disorders are depression, addiction, post-traumatic stress disorder and/or personality disorders.

In a preferred embodiment, the kit of the present invention can be used for the treatment and/or prevention of neurological disorders. Preferably, the neurological disorder is acquired brain injury, ataxia, brain tumor, dementia, dystonia, epilepsy, functional and dissociative neurological symptoms, meningitis, motor neuron disease, multiple sclerosis, muscular dystrophy, myalgic encephalomyelitis, Parkinson's disease, progressive supranuclear palsy, Huntington's disease, spina bifida, hydrocephalus, spinal injury, stroke, Tourette syndrome and/or transverse myelitis. More preferably, the neurological disorders are neurodegenerative and/or vascular dementias.

In a preferred embodiment, the kit of the present invention can be used for the treatment and/or prevention Parkinson's Disease and/or Alzheimer's disease. Preferably, the kit of the present invention can be used for the treatment and/or prevention Parkinson's Disease.

Administration

A compound described by formula (I) and a 5-HT2A receptor antagonist may be administered together or separately to an individual who suffers from one or more psychiatric and/or neurological disorders and/or who is at risk of suffering from one or more psychiatric and/or neurological disorders.

In a preferred embodiment, a compound described by formula (I) may be administered to an individual who is already being administered a 5-HT2A receptor antagonist and who is suffering from one or more psychiatric and/or neurological disorders and/or who is at risk of suffering from one or more psychiatric and/or neurological disorders. Conversely, in an alternative embodiment, a 5-HT2A receptor antagonist may be administered to an individual who is already being administered a compound described by formula (I) and who is suffering from one or more psychiatric and/or neurological disorders and/or who is at risk of suffering from one or more psychiatric and/or neurological disorders.

In a preferred embodiment, the administration of the combination product to an individual who is suffering from one or more psychiatric and/or neurological disorders and/or who is at risk of suffering from one or more psychiatric and/or neurological disorders causes no hallucinogenic and/or psychedelic side effects and/or less hallucinogenic and/or psychedelic side effects than if the 5-HT2A receptor antagonist had not been administered.

In a preferred embodiment, the 5-HT2A receptor antagonist present in the combination product alleviates and/or eliminates the hallucinogenic and/or psychedelic side effects caused by a compound described by formula (I).

In a preferred embodiment, the individual who is already being administered a 5-HT2A receptor antagonist and who is suffering from one or more psychiatric and/or neurological disorders and/or who is at risk of suffering from one or more psychiatric and/or neurological disorders will present no or less hallucinogenic and/or psychedelic side effects upon the administration of a compound described by formula (I) than if the individual had not already been administered a 5-HT2A receptor antagonist.

In a preferred embodiment, the individual who is already being administered a compound described by formula (I) and who is suffering from one or more psychiatric and/or neurological disorders and/or who is at risk of suffering from one or more psychiatric and/or neurological disorders will present no or less hallucinogenic and/or psychedelic side effects upon the administration of a 5-HT2A receptor antagonist than if the individual had not been administered a 5-HT2A receptor antagonist.

In a preferred embodiment, the combination product is administered to prevent the onset of a neurological and/or psychiatric disorder. For example, the combination product can be administered to an individual who is at risk of developing one or more psychiatric and/or neurological disorders.

In a preferred embodiment, the combination product is administered to treat a neurological and/or psychiatric disorder. For example, the combination product can be administered to an individual who suffers from one or more psychiatric and/or neurological disorders.

In a preferred embodiment, the administration of the combination product to an individual stimulates the proliferation, migration and/or differentiation of neural stem cells. In a preferred embodiment, the administration of the combination product to an individual stimulates the proliferation and/or differentiation of neural stem cells.

In a preferred embodiment, the individual who is already being administered a 5-HT2A receptor antagonist and is then administered a compound described by formula (I) will have the compound described by formula (I) stimulate the proliferation and/or differentiation of neural stem cells. In a preferred embodiment, the individual who is already being administered a compound described by formula (I) and is then administered a 5-HT2A receptor antagonist will have the compound described by formula (I) stimulate the proliferation and/or differentiation of neural stem cells.

In a preferred embodiment, the combination product is prepared for oral, sublingual, buccal, intranasal, intravenous, intramuscular, subcutaneous, rectal, transdermal, topical and/or inhalation-mediated administration routes, preferably oral, sublingual, inhalation-mediated and/or intranasal routes.

The present application also provides the following items:

[1] A pharmaceutical combination product comprising:
(i) a compound described by the following formula (I):

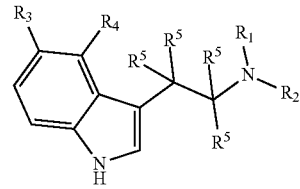

wherein R1 is selected from the group consisting of methyl, ethyl, n-propyl, allyl and isopropyl;
wherein R2 is selected from the group consisting of methyl, ethyl, n-propyl, allyl and isopropyl;
wherein R3 is selected from the group consisting of hydrogen, methoxy, methyl, hydroxy and a halogen; and
wherein R4 is selected from the group consisting of hydrogen, hydroxy, phosphoryloxy and acetoxy;
wherein R5 is selected from the group consisting of deuterium ($^2$H) and protium ($^1$H); and
(ii) a 5-HT2A receptor antagonist.

[2] The combination product according to item 1 wherein the compound described by formula (I) is selected from the group consisting of N,N-dimethyltryptamine, N,N-diethyltryptamine, N,N-dipropyltryptamine and 5-methoxy-N,N-dimethyltryptamine.

[3] The combination product according to any one of items 1-2 wherein the 5-HT2A receptor antagonist is selected from the group consisting of Methiothepin, Ketanserin, Flibanserin, Methysergide, Trazodone, Nefazodone, Cinitapride, Cyproheptadine, Brexpiprazole, Cariprazine, Agomelatine, Pimavanserin, Eplivanserin, Volinanserin, Altanserin, Setoperone, Ritanserin, LY-367,265, 1-(1-Naphthyl)piperazine, SB 206553, Pirenperone, SB-215505, Metergoline, Deramciclane, Amperozide, Glemanserin, 5-MeO-NBpBrT, Adatanserin, AMDA, Cinanserin, Fananserin, Iferanserin, AC-90179, LY86057, GSK-215083, Cyamemazine, Mesulergine, BF-1, LY215840, Sergolexole, Spiramide, LY53857, Amesergide, LY108742, Pipamperone, LY314228 and 5-I-R91150.

[4] The combination product according to any one of items [1]-[3] which further comprises a monoamine oxidase inhibitor.

[5] The combination product according to any one of items [1]-[4] wherein the combination product is a composition, or the compound described by formula (I) and the 5-HT2A receptor antagonist are physically separated.

[6] The combination product according to any one of items [1]-[4] wherein the combination product comprises:
(a) a compound described by formula (I) and instructions on how to administer the compound described by formula (I) with a 5-HT2A receptor antagonist; or
(b) a 5-HT2A receptor antagonist and instructions on how to administer the 5-HT2A receptor antagonist with a compound described by formula (I).

[7] The combination product according to any one of items [1]-[6] wherein the combination product is prepared for oral, sublingual, buccal, intranasal, intravenous, intramuscular, subcutaneous, rectal, transdermal, topical and/or inhalation-mediated administration.

[8] The combination product according to any one of the preceding items for use as a medicament.

[9] The combination product according to any one of items [1]-[7] for use in the treatment and/or prevention of psychiatric and/or neurological disorders.

[10] The combination product according to item 9 for use in the treatment and/or prevention of a disorder selected from the group consisting of acquired brain injury, ataxia, brain tumor, dementia, dystonia, epilepsy, functional and dissociative neurological symptoms, meningitis, motor neuron disease, multiple sclerosis, muscular dystrophy, myalgic encephalomyelitis, Parkinson's disease, progressive supranuclear palsy, Huntington's disease, Alzheimer's disease, fronto-temporal dementia, vascular dementia, cognitive decline associated with aging, spina bifida, hydrocephalus, spinal injury, stroke, Tourette syndrome, transverse myelitis, panic disorder, agoraphobia, social anxiety disorder, phobias, post-traumatic stress disorder, obsessive compulsive disorder, generalized anxiety disorder, bipolar disorder, depression, anorexia nervosa, binge eating disorder, bulimia nervosa, psychosis, schizophrenia, substance addiction and personality disorders.

[11] A kit for the treatment and/or prevention of psychiatric and/or neurological disorders comprising the combination product according to any one of items 1-7.

[12] The combination product for use according to any one of items [8]-[10], wherein the 5-HT2A receptor antagonist alleviates or eliminates the hallucinogenic and/or psychedelic side effects caused by the compound described by formula (I).

[13] The combination product for use according to any one of items [8]-[10], wherein the compound described by formula (I) stimulates the proliferation and/or differentiation of neural stem cells.

[14] The combination product for use according to any one of items 8-10, wherein the combination product is administered at least two times, preferably more than two times.

EXAMPLES

Example 1: DMT reduces the undifferentiated state of neural stem cells via the Sigma-1 receptor. This effect is maintained in the presence of 5-HT2A antagonists.

Results from this example are shown in FIG. 1. Neural stem cells were established as primary cultures obtained from adult mice (2-3 month old) by isolation of the subgranular neurogenic niche and seeded into 6-well dishes at a density of ~40,000 cells per $cm^2$ in DMEM/F12 (1:1, Invitrogen) containing 10 ng/mL EGF, 10 ng/mL FGF and N2 medium (Gibco, Madrid, Spain). Neurospheres were treated under proliferative conditions (culture medium containing 10 ng/mL EGF and 10 ng/mL FGF (Gibco, Madrid, Spain)) with saline, DMT (1 μM) alone, DMT+Methiothepin (Met, a mixed 5-HT2A/5-HT1A receptor antagonist; 1 μM), DMT+BD1063 (BD, a selective Sigma-1 receptor antagonist; 1 μM), DMT+Ritanserin (Rit, a selective 5-HT2A receptor antagonist, 1 μM) and DMT+WAY100635 (WAY, a selective 5-HT1A receptor antagonist, 1 μM) for 7 days. Methiothepin mesylate (Catalog number M149), BD1063 dihydrochloride (Catalog number SML0276) and Ritanserin (Catalog number R103) were purchased from Sigma (Madrid, Spain). WAY100635 maleate (Catalog number ab120550) was purchased from Abcam (Cambridge, UK). Proteins were quantified using Western blots. Differentiated cultured neurospheres were re-suspended in ice-cold cell lysis buffer (Cell Signaling Technology) with protease inhibitor cocktail (Roche) and incubated for 15-30 min on ice. A total amount of 30 μg of protein was loaded on a 10% or 12% SDS-PAGE gel and transferred onto nitrocellulose membranes (Protran, Whatman). The membranes were blocked in Tris-buffered saline with 0.05% Tween-20 and 5% skimmed milk, incubated with primary and secondary antibodies, and washed according to standard procedures. Primary antibodies used were purchased from Abcam (Cambridge, United Kingdom): anti-musashi (Catalog number 52865), anti-nestin (Catalog number 2Q178) and SOX-2 (2Q178 97959). Secondary antibodies were purchased from Jackson ImmunoResearch Laboratories (West Grove, Pa., USA): Peroxidase-conjugated AffiniPure rabbit Anti-Mouse IgG (H+L)(Catalog number 315-035-003) and peroxidase-conjugated AffiniPure Goat Anti-rabbit IgG (H+L)(Catalog number 111-035-003).

To study the "stemness" of cultured neurospheres, we analyzed the expression of the following proteins: a) musashi-1, a marker of undifferentiation; b) nestin, an intermediate filament protein characteristic of neural stem/progenitor cells; and c) "sex determining region Y-box 2" (SOX-2), a transcription factor essential for maintaining self-renewal and pluripotency of undifferentiated stem cells. We treated the neurosphere cultures for 7 days with DMT alone or in combination with each of the antagonists mentioned above, all at 1 μM concentration. After treatment, we isolated the proteins and performed Western blots.

FIG. 1 clearly shows the measured amounts of musashi-1, nestin and SOX-2 in the neurospheres following treatment with DMT alone and in combinations with each antagonist. DMT significantly reduced the levels of all three proteins.

These results indicate that compared to saline, DMT promotes a loss of "stemness", i.e., a departure from the undifferentiated state that characterizes neural progenitors, in vitro. Furthermore, while this effect was blocked by the Sigma-1 receptor antagonist BD1063 (BD), it was not blocked by the mixed 5-HT1A/2A receptor antagonist methiothepin (Met), the selective 5-HT2A receptor antagonist ritanserin (Rit), or the selective 5-HT1A receptor antagonist WAY100635 (WAY).

Example 1 demonstrates: a) The novel and unexpected finding that DMT induces a departure from the undifferentiated state or "stemness" in neural progenitor cells; b) The novel and unexpected finding that DMT reduces "stemness" through its interaction with the Sigma-1 receptor; c) The novel and unexpected finding that DMT-induced reductions in "stemness" are not mediated by the 5-HT1A receptor (WAY); d) The innovative finding that DMT-induced reductions in "stemness" are preserved when this hallucinogenic tryptamine is combined with a mixed (Met) or a selective (Rit) 5-HT2A receptor antagonist. Since 5-HT2A antagonists are known to block the side effects of hallucinogenic tryptamines in humans, this example shows the viability of stimulating endogenous progenitor cell niches by combining a hallucinogenic tryptamine (in this example DMT), with a 5-HT2A antagonist (in this example Met or Rit). The combination of DMT with either a mixed or a selective 5-HT2A antagonist preserves the desired beneficial effects of the tryptamine while simultaneously blocking the receptor known to be responsible for the hallucinogenic side effects of tryptamines in humans.

Example 2: DMT promotes neurosphere formation via the Sigma-1 receptor. This effect is maintained in the presence of 5-HT2A antagonists.

Results from this example are shown in FIG. 2. Free floating neurospheres were grown under proliferative conditions and administered saline (control), DMT (1 μM), DMT+methiothepin (Met, a mixed 5-HT2A/5-HT1A receptor antagonist, 1 μM), DMT+BD1063 (BD, a selective Sigma-1 receptor antagonist, 1 μM), Ritanserin (Rit, a selective 5-HT2A receptor antagonist, 1 μM) and WAY100635 (WAY, a selective 5-HT1A receptor antagonist, 1 μM) for 7 days as mentioned above (please see Example 1 for detailed information on vendors and catalog numbers of the antagonists used). Number and diameter of neurospheres were scored using the Nikon Digital Sight, SD-L1 software (Nikon, Japan). Ten wells per condition were tested and experiments were counted.

FIG. 2 shows that addition of the DMT to the cultures markedly increased formation and the size of the neurospheres. After 7 days of DMT treatment, the number of neurospheres was significantly higher than in the vehicle-treated cultures. DMT also increased significantly the size of the neurospheres as compared with vehicle/treated cultures. These results indicate that DMT stimulated the multiplication of neural progenitors obtained from the hippocampal neurogenic niche of adult animals. Furthermore, as depicted in the figure, DMT-induced effects were blocked by the Sigma-1 receptor antagonist BD1063 (BD), but not by the mixed 5-HT1A/2A receptor antagonist methiothepin (Met), the selective 5-HT2A receptor antagonist ritanserin (Rit), or the selective 5-HT1A receptor antagonist WAY100635 (WAY).

Example 2 demonstrates: a) The novel and unexpected finding that DMT promotes neurosphere formation, as measured by the generation of neurospheres (size and number); b) The novel and unexpected finding that DMT-induced increases in neurosphere formation (size and number) are mediated by stimulation of the Sigma-1 receptor; c) The novel and unexpected finding that DMT-induced increases in neurosphere formation are not mediated by the 5-HT1A receptor (WAY); d) The innovative finding that DMT-induced increases in neurosphere formation are preserved when this hallucinogenic tryptamine is combined with a mixed (Met) or selective (Rit) 5-HT2A antagonist. Since 5-HT2A antagonists are known to block the side effects of hallucinogenic tryptamines in humans, this example further support the viability of stimulating endogenous neurogenic niches by combining a hallucinogenic tryptamine (in this example DMT), with a 5-HT2A antagonist (in this example both Met and Rit). The combination of DMT with either a mixed or a selective 5-HT2A antagonist allows the retention of the beneficial effects of the tryptamine while simultaneously blocking the receptor known to be responsible for its hallucinogenic side effects in humans.

The combination of DMT with either a mixed or a selective 5-HT2A antagonist preserves the desired beneficial effects of the tryptamine while simultaneously blocking the receptor known to be responsible for the hallucinogenic side effects of tryptamines in humans.

Example 3: DMT promotes neural stem cell proliferation via the Sigma-1 receptor. This effect is maintained in the presence of 5-HT2A antagonists.

Results from this example are shown in FIG. 3. Changes in the levels of protein Ki67, a marker of actively dividing cells, were assessed using: a) fluorescence immunodetection by means of immunocytochemistry analysis and a primary Ki67 antibody; and b) quantification of Ki67 protein levels by immunoblot analysis using the methodology described in Example 1. For the immunocytochemistry analysis, neurospheres grown on glass cover slides were fixed for 15 minutes at room temperature in 4% paraformaldehyde and then incubated at 37° C. for 1h with a primary antibody directed against ki67 (rabbit, Abcam). After several rinses in PBS, samples were incubated with an Alexa-488 goat anti-rabbit antibody (Molecular Probes, Madrid, Spain) for 45 min at 37° C. Staining of cell nuclei was performed using 4',6-diamidino-2-phenylindole (DAPI). Finally, images were acquired in a LSM710 laser scanning spectral confocal microscope (Zeiss, Madrid, Spain). Confocal microscope settings were adjusted to produce the optimum signal-to-noise ratio. The Ki67 protein is strictly associated with cell proliferation. Ki67 staining is an excellent marker for determining the so-called "growth fraction" of a given cell population. Neurospheres had been previously treated with vehicle, DMT or a combination of DMT and each of the three antagonists tested (please see Example 1 for detailed information on vendors and catalog numbers of the antagonists used).

FIG. 3 shows that addition of the DMT to the cultures resulted in an increase in the number of Ki67-positive cells indicating a direct effect of DMT on proliferation. While this effect was blocked by the Sigma-1 receptor antagonist BD1063 (BD), it was not blocked by the mixed 5-HT1A/2A receptor antagonist methiothepin (Met), the selective 5-HT2A receptor antagonist ritanserin (Rit), or the selective 5-HT1A receptor antagonist WAY100635 (WAY).

Example 3 demonstrates: a) The novel and unexpected finding that DMT has a direct effect on cell proliferation, as measured by the increase in the levels of the proliferation marker protein ki67; b) The novel and unexpected finding that DMT-induced increases in proliferation are mediated by stimulation of the Sigma-1 receptor; c) The novel and unexpected finding that DMT-induced increases in proliferation are not mediated by the 5-HT1A receptor (WAY); d)

The innovative finding that DMT-induced increases in proliferation are preserved when this hallucinogenic tryptamine is combined with a mixed (Met) or selective (Rit) 5-HT2A antagonist. Since 5-HT2A antagonists are known to block the side effects of hallucinogenic tryptamines in humans, this example further support the viability of stimulating endogenous neurogenic niches by combining a hallucinogenic tryptamine (in this example DMT), with a 5-HT2A antagonist (in this example both Met and Rit). The combination of DMT with either a mixed or a selective 5-HT2A antagonist allows retaining the beneficial effects of the tryptamine while simultaneously blocking the receptor known to be responsible for its hallucinogenic side effects in humans.

Example 4: DMT promotes stem cell differentiation of neural stem cells into neural and glial phenotypes. This Effect is Maintained in the Presence of 5-HT2A antagonists.

Results from this example are shown in FIG. 4. Neurosphere cultures were obtained as described above and subsequently kept under differentiation conditions (in the absence of EGF and FGF but in the presence of 1% fetal bovine serum). To that purpose, neurospheres were seeded onto poly-L-lysine (P4707, Sigma) pre-coated coverslips and cultured for 3 days in the presence of DMT (1 µM), DMT+methiothepin (a mixed 5-HT2A/5-HT1A antagonist, 1 µM), DMT+BD1063 (a selective Sigma-1 antagonist, 1 µM), DMT+Ritanserin (a selective 5-HT2A antagonist, 1 µM) and DMT+WAY100635 (a selective 5-HT1A antagonist, 1 µM) (please see Example 1 for detailed information on vendors and catalog numbers of the antagonists used). After 3 days in culture, the adhered neurospheres were fixed for 15 minutes at room temperature in 4% paraformaldehyde and incubated at 37° C. for 1h with primary antibodies directed against the neuronal markers β-III-tubulin (TuJ-1 clone; rabbit; Abcam) and MAP-2 (mouse; Sigma); the oligodendrocyte marker CNPase (rabbit, Covance) and the astroglial marker GFAP (mouse; Sigma). β-III-tubulin is a protein of the tubulin family found exclusively in neurons. It allows for the identification of neurons in samples of brain tissue. MAP-2 (microtubule-associated protein 2) is also present only in neurons. β-III-tubulin and MAP-2 are not expressed in glial cells. Their presence in this experiment revealed differentiation of neural progenitors into a neuronal phenotype. CNPase is a myelin-associated enzyme and in the central nervous system is expressed exclusively by oligodendrocytes. Its presence in this experiment revealed the differentiation of neural progenitors into oligodendrocytes. GFAP (glial fibrillary acidic protein) is a protein found in glial cells, especially astrocytes. Its presence in this experiment revealed differentiation of neural progenitors into astrocytes. After several rinses with PBS, samples were then incubated with Alexa-488 goat anti-rabbit and Alexa-647 goat anti-mouse antibodies (Molecular Probes, Madrid, Spain) for 45 min at 37° C. Staining of nuclei was performed using 4',6-diamidino-2-phenylindole (DAPI). Finally, images were acquired in a LSM710 laser scanning spectral confocal microscope (Zeiss, Madrid, Spain). Confocal microscope settings were adjusted to produce the optimum signal-to-noise ratio. Quantification of the protein levels for each marker was performed using immunoblot analysis, following the same method described in the previous examples.

FIG. 4 shows that DMT promoted differentiation of neural progenitors into neural and glial phenotypes. This was evidenced by the increase in the expression of the two neuronal markers (Tuj1 & MAP-2), the oligodendrocyte marker (CNPase), and the astrocyte marker (GFAP). While the effects of DMT on differentiation were blocked by the Sigma-1 receptor antagonist BD1063 (BD), they were not blocked by the mixed 5-HT1A/2A receptor antagonist methiothepin (Met), the selective 5-HT2A receptor antagonist ritanserin (Rit), or the selective 5-HT1A receptor antagonist WAY100635 (WAY).

Example 4 demonstrates: a) The novel and unexpected finding that DMT promotes the differentiation of neural stem cells into neurons and glial cells; b) The novel and unexpected finding that DMT-induced differentiation is mediated by stimulation of the Sigma-1 receptor; c) The novel and unexpected finding that DMT-induced increases in differentiation are not mediated by the 5-HT1A receptor (WAY); d) The innovative finding that DMT-induced increases in differentiation are preserved when this hallucinogenic tryptamine is combined with a mixed (Met) or selective (Rit) 5-HT2A antagonist. Since 5-HT2A antagonists are known to block the side effects of hallucinogenic tryptamines in humans, this example demonstrates that neurogenesis can be obtained by administering a combination of a hallucinogenic tryptamine (in this example DMT), with a 5-HT2A antagonist (in this example both Met and Rit). The combination of DMT with either a mixed or a selective 5-HT2A antagonist allows for the retention of the beneficial effects of the tryptamine while simultaneously blocking the receptor known to be responsible for its hallucinogenic side effects in humans.

Example 5: DMT activates the hippocampal subgranular neurogenic niche in vivo via the Sigma-1 receptor. This effect is maintained in the presence of a 5-HT2A antagonist, and is independent from 5-HT1A stimulation by DMT.

Results from this example are shown in FIG. 5. Adult male C57BL/6 mice (obtained from Charles River Labs) were injected in the lateral ventricle (coordinates: from bregma, posterior −1 mm, lateral +1.3 mm, ventral +2 mm, according to the atlas of Paxinos and Franklin (Paxinos G, Franklin KBJ. *The Mouse Brain in Stereotaxic Coordinates*. 4. San Diego: Academic Press; 2012)), using a stereotaxic apparatus (Kopf Instruments, CA) with DMT (0.1 µg/animal), alone or in combination with the selective Sigma-1 BD1063 (BD, 0.2 µg/animal, Sigma, catalog number SML0276), the mixed 5-HT2A/1A receptor antagonist methiothepin (Met, 0.2 µg/animal, Sigma catalog number M149), or the selective 5-HT1A receptor antagonist WAY100635 (WAY, 0.2 µg/animal, ABCAM catalog number ab120550). Prior to the injection, mice were anesthetized by intraperitoneal injection of ketamine (60 mg/kg) and medetomidine (0.125 mg/kg). After four days, animals were intraperitoneally injected with the proliferation marker 5-bromo-2-deoxyuridine (BrdU, 50 mg/kg, Sigma-B5002) and sacrificed on day 5. Following anesthesia, the animals were perfused transcardially with 4% paraformaldehyde, and brains were obtained, post-fixed in the same solution at 4-8° C. overnight, cryoprotected, frozen, and finally 30 µm coronal sections were obtained in a cryostat. Free-floating sections were immunostained using immunofluorescence analysis. For BrdU detection, samples were first incubated with 2 M HCl for 30 minutes at 37° C. before blocking 1 hour in PBS containing 5% normal serum, 0.1 M lysine, and 0.1% Triton X-100. Sections were then incubated with anti-BrdU mouse monoclonal antibody (DAKO, Barcelona) combined with an anti-nestin rabbit antibody (Abcam, Cambridge, UK) or an anti-double courtin (DCX) goat antibody (Santa Cruz Biotech. USA) at 4° C. overnight, washed three times and incubated with Alexa Fluor-488 goat anti-mouse and Alexa 647-goat anti-rabbit or -horse anti-goat secondary antibodies (Molecular Probes, Madrid, Spain), respectively, for 1 hour at room temperature. After rinses, sections were mounted with Vectashield. Images were obtained using a LSM710 laser scanning spectral confocal microscope (Zeiss, Madrid, Spain). Confocal microscope settings were adjusted to produce the optimum signal-to-noise ratio. A modified stereological approach was used to estimate the total numbers of cells stained with BrdU/Nestin double immunofluorescence (Morales-Garcia et al., 2017, *Stem Cells* 35:458-472). Confocals were viewed and captured under a ×63 objective to avoid oversampling errors. From serial coronal sections (30 mm) from the entire rostrocaudal extent of the dentate gyrus (DG), every sixth section was selected to count the number of immunoreactive cells. The boundaries of these nervous system regions were determined with reference to internal anatomic landmarks (Paxinos G, Franklin KBJ. The Mouse Brain in Stereotaxic Coordinates. 4. San Diego: Academic Press; 2012). For DG area selection, images were analyzed using computer-assisted image analysis software (Soft Imaging System Corporation, Lakewood, Colo., http://www.soft-imaging.com). Positive cells, which intersected the uppermost focal plane (exclusion plane) and the lateral exclusion boundaries of the counting frames, were not counted. Six animals per group were used. The results were expressed as the total number of labeled cells in the DG of the hippocampus by multiplying the average number of labeled cells/DG by the total number of 30 mm thick-sections containing the DG.

FIG. 5 shows that DMT induced proliferative effects also occurred when administered in vivo as shown by increases BrdU in staining (white areas), stimulating migration of the newly created neuroblasts. Note that the stimulatory effects were completely blocked by the Sigma-1 antagonist BD1063, but not by the mixed 5-HT1A/2A receptor antagonist methiothepin (Met) or the selective 5-HT1A receptor antagonist WAY100635.

Example 5 demonstrates: a) The novel and unexpected finding that DMT stimulates neurogenic niches and promotes neurogenesis in vivo in live adult animals; b) The novel and unexpected finding that DMT-induced in vivo neurogenesis is mediated through the Sigma-1 receptor; c) The novel and unexpected finding that DMT-induced effects are not mediated by the 5-HT1A receptor (the effects were preserved in the presence of the mixed 5-HT2A/1A receptor antagonist methiothepin, or the selective 5-HT1A receptor antagonist WAY100635); d) The innovative finding that DMT-induced effects are also preserved in vivo when this hallucinogenic tryptamine is combined with a 5-HT2A antagonist, and that this effect is not mediated by DMT stimulation of the 5-HT1a receptor. Since 5-HT2A antagonists are known to block the side effects of hallucinogenic tryptamines in humans, this example demonstrates that stimulation of the hippocampal neurogenic niche can be attained in vivo by administering a combination of a hallucinogenic tryptamine (in this example DMT), with a 5-HT2A antagonist (in this example the mixed 5-HT2A/1A receptor antagonist methiothepin (Met)). Similar to what was found in the previous in vitro examples using neurospheres, the combination of DMT with a 5-HT2A antagonist allowed for the retention of the beneficial effects of the tryptamine in vivo, while simultaneously blocking the receptor known to be responsible for its hallucinogenic side effects in humans. The therapeutic effect is still obtainable even if the 5-HT2A antagonist is not completely selective and displays 5-HT1A antagonism.

Example 6: DMT Promotes In Vivo Neurogenesis in the Subgranular Zone of the Hippocampus Via the Sigma-1 Receptor. This Effect is Maintained in the Presence of a 5-HT2A Antagonist, and is Independent from 5-HT1A Stimulation by DMT.

Results from this example are summarized in FIG. 6. Adult male C57BL/6 mice (obtained from Charles River Labs, Barcelona, Spain) were injected every other day for 3 weeks with DMT (0.1 μg/animal), alone or in combination with the selective Sigma-1 BD1063 antagonist (BD, 0.2 μg/animal, Sigma, Catalog number SML0276), the mixed 5-HT2A/1A receptor antagonist methiothepin (Met, 0.2 μg/animal, Sigma, Catalog number M149), or the selective 5-HT1A receptor antagonist WAY100635 (WAY, 0.2 μg/animal, ABCAM catalog number ab120550). On day 1 of treatment, animals were intraperitoneally injected with the proliferation marker 5-bromo-2-deoxyuridine (BrdU, 50 mg/kg, Sigma, Catalog number B5002) and sacrificed on day 21. Following anesthesia, the animals were perfused transcardially with 4% paraformaldehyde, and the brains obtained and post-fixed in the same solution at 4-8° C. overnight. They were subsequently cryoprotected, frozen, and finally cut into 30 μm coronal sections in a cryostat. Free-floating sections were immunostained using immunofluorescence analysis. For BrdU detection, samples were first incubated with 2 M HCl for 30 minutes at 37° C. before blocking 1 hour in PBS containing 5% normal serum, 0.1 M lysine, and 0.1% Triton X-100. Sections were then incubated with anti-BrdU mouse monoclonal antibody (DAKO, Barcelona, Spain, Catalog number M0744) combined with a neuronal marker, anti-neuN rabbit antibody (Abcam, Cambridge, UK. Catalog number ABN78) or an anti-double courtin (DCX) goat antibody (Santa Cruz Biotech. USA) at 4° C. overnight, washed three times and incubated with Alexa Fluor-488 goat anti-mouse and Alexa 647-goat anti-rabbit or -horse anti-goat secondary antibodies (Molecular Probes, Madrid, Spain), respectively, for 1 hour at room temperature. After rinses, sections were mounted with Vectashield. Images were obtained using a LSM710 laser scanning spectral confocal microscope (Zeiss, Madrid, Spain). Confocal microscope settings were adjusted to produce the optimum signal-to-noise ratio FIG. 6 shows that DMT promotes in vivo the generation of new neurons as indicated by an increase in double BrdU-NeuN stained cells (shown in white against the black background). Note that the neurogenic effect was blocked by the Sigma-1 antagonist BD1063, but not by the mixed 5-HT2A/1A receptor antagonist methiothepin (Met), or the selective 5-HT1A receptor antagonist WAY100635 (WAY).

Example 6 demonstrates: a) The novel and unexpected finding that DMT stimulates neurogenic niches and promotes neurogenesis in vivo in live adult animals; b) The novel and unexpected finding that DMT-induced in vivo neurogenesis is mediated through the Sigma-1 receptor; c) The novel and unexpected finding that DMT-induced effects are not mediated by the 5-HT1A receptor (the effects were preserved in the presence of the mixed 5-HT2A/1A receptor antagonist methiothepin, or the selective 5-HT1A receptor antagonist WAY100635); d) The innovative finding that DMT-induced effects are also preserved in vivo when this hallucinogenic tryptamine is combined with a 5-HT2A antagonist. Since 5-HT2A antagonists are known to block the side effects of hallucinogenic tryptamines in humans, this example demonstrates that stimulation of the hippocampal neurogenic niche and full neurogenesis can be attained in vivo by administering a combination of a hallucinogenic tryptamine (in this example DMT), with a 5-HT2A antagonist (in this example the mixed 5-HT2A/1A receptor antagonist methiothepin (Met)). Similar to what was found in the previous in vitro examples using neurospheres cultured in vitro, the combination of DMT with a 5-HT2A antagonist allowed for the retention of the beneficial effects of the tryptamine in vivo, while simultaneously blocking the receptor known to be responsible for its hallucinogenic side effects in humans. The therapeutic effect is still obtainable even if the 5-HT2A antagonist is not completely selective and displays 5-HT1A antagonism.

Example 7: The hallucinogenic tryptamines DPT, 5-MeO-DMT and DET promote in vitro the differentiation into neurons of adult neural stem cells derived from the subgranular zone of the hippocampus. This effect is maintained in the presence of a 5-HT2A antagonist. Results from this example are shown in FIG. 7. Neurosphere cultures were isolated as described in Example 1 the and cultured in the presence of DPT or 5-MeO-DMT or DET (1 µM) alone or in combination with Ritanserin (a selective 5-HT2A antagonist, 1 µM). DPT, 5-MeO-DMT and DET where obtained by chemical synthesis conducted at our request by a local Pharmaceutical Chemistry Laboratory. Ritanserin (Rit) was purchased from a commercial source (detailed information on vendor and catalog number is provided in Example 1). Cultures were kept under differentiation conditions as described in Example 4. In the combined treatments, Rit was added to the medium 1h prior to tryptamine administration. Each tryptamine (alone or in combination with Rit) were administered every other day. After 3 days in culture, the adhered neurospheres were fixed for 15 minutes at room temperature in 4% paraformaldehyde and incubated at 37° C. for 1h with primary antibodies directed against the neuronal markers β-III-tubulin (TuJ-1 clone; rabbit; Abcam) and MAP-2 (microtubule-associated protein 2; mouse; Sigma). Both markers are widely used to selectively label neurons and thus identify their presence in media containing also other cell types. After incubation with antibodies and following several rinses with PBS, samples were incubated with Alexa-488 goat anti-rabbit and Alexa-647 goat anti-mouse antibodies (Molecular Probes) for 45 min at 37° C. Staining of nuclei was performed using 4',6-diamidino-2-phenylindole (DAPI). Finally, images were acquired in a LSM710 laser scanning spectral confocal microscope (Zeiss, Madrid, Spain). Confocal microscope settings were adjusted to produce the optimum signal-to-noise ratio. The positive identification of neurons in this experiment demonstrated that neural stem cells had undergone differentiation into neurons. At least eight neurospheres per condition over three independent experiments were used. Quantification of the protein levels for each marker was performed using immunoblot analysis, following the same method described in the previous examples.

FIG. 7 shows that DPT, 5-MeO-DMT, and DET promoted differentiation of neural stem cells into neurons. This was evidenced by the increase in the expression of the two neuronal markers Tuj1 and MAP-2. This effect was maintained for all three compounds in the presence of the selective 5-HT2A receptor antagonist Ritanserin.

Example 7 demonstrates: a) The novel and unexpected finding that the hallucinogenic tryptamines DPT, 5-MeO-DMT and DET promote the differentiation of neural stem cells into neurons; b) The fact that the neurogenic effects previously found for DMT are not exclusive of this compound, but extend to other hallucinogenic tryptamines; c) The innovative finding that, as demonstrated for DMT, the neurogenic effects of other hallucinogenic tryptamines (in this example DPT, 5-MeO-DMT and DET) are preserved when they are combined with a 5-HT2A antagonist. Since 5-HT2A antagonists block the side effects of hallucinogenic tryptamines in humans, this example demonstrates that neurogenesis can be obtained by administering a combination of a hallucinogenic tryptamine that can be different from, with a 5-HT2A antagonist. The combination of a hallucinogenic tryptamine with a 5-HT2A antagonist allows for the retention of the beneficial effects of the tryptamine while simultaneously blocking the receptor known to be responsible for their hallucinogenic side effects in humans.

Example 8: DMT, DET, DPT and 5-MeO-DMT administration in vitro prevents inflammation in rat primary glial cells. This effect is maintained in the presence of a 5-HT2A antagonist. Results from this example are shown in FIG. 8. Rat primary glial cell cultures were prepared from the cerebral cortex of 3 day old rats which were dissected, dissociated, and incubated with 0.25% trypsin/EDTA at 37° C. for 1 h. After centrifugation, the pellet was washed three times with HBSS (Gibco) and the cells were plated in poly-D-lysine (20 µg/mL) pretreated flasks (75 cm2). After 7-10 days, the flasks were agitated in an orbital shaker for 4 h at 230 rpm at 37° C. and non-adherent microglial cells were isolated and plated. Then Dulbecco's Modified Eagle's Medium (DMEM) was added to the flasks, which were agitated in a horizontal shaker at 260 rpm at 37° C. After overnight agitation, the supernatant (oligodendrocytes and some remaining microglial cells) was removed, and astrocytes (adherent cells) were collected. The purity of the cultures was >95%, as determined by immunofluorescence analysis using an anti-glial fibrillary acidic protein (GFAP; clone G-A-5; Sigma-Aldrich) antibody to identify astrocytes, and an anti-Iba1 (Wako Catalog No. 019-19741) antibody to identify microglial cells. On attaining semiconfluence, cells were administered each of the test tryptamines at 1 µM or with the combination test tryptamine+Ritanserin (Rit at 1 µM) 2 h before exposure to lipopolysaccharide (LPS, 10 µg/mL; Sigma-Aldrich) and kept in the presence of each drug or drug combination for 24 h. In combination studies, Rit was added to medium 1h before administration of the corresponding tryptamine. Vehicle-treated cultures were used as a control. After the 24 h drug exposure period, cultures were tested to assess nitrite release. To quantify nitrite concentrations in culture medium, supernatants of glial cultures were collected and mixed with an equal volume of Griess reagent (Sigma-Aldrich). Samples were then incubated at room temperature for 15 min and absorbance was measured at 540 nm on a microplate reader. Results are expressed as the mean±SEM of six replications in three different experiments FIG. 8 shows that LPS induced an inflammatory process in both microglial and astrocyte cell cultures, as indicated by the increases in nitrite levels in vehicle treated cultures. Pre-treatment with DMT, DPT, 5-MeO-DMT, and DET displayed antiinflammatory effects. This was evidenced by the significant decreases in nitrite levels obtained for all four tryptamines tested. The antiinflammatory effect was maintained for all four compounds promoted differentiation of neural stem cells into neurons. This was evidenced by the increase in the expression of the two neuronal markers Tuj1 and MAP-2. This effect was maintained for all three compounds in the presence of the selective 5-HT2A receptor antagonist Ritanserin.

Example 8 demonstrates: a) The novel and unexpected finding that DMT, DET, DPT and 5-MeO-DMT display antiinflammatory effects on microglial cells and astrocytes at the same concentration at which they promote neurogenesis. b) The innovative finding that the observed antiinflammatory effects are preserved when they are combined with a 5-HT2A antagonist. Since 5-HT2A antagonists block the side effects of hallucinogenic tryptamines in humans, the proposed drug combination would retain the desired antiinflammatory effects on glial cells, while simultaneously blocking the receptor known to be responsible for their hallucinogenic side effects in humans. Thus, it is plausible that the combination product could be used to treat diseases such as Alzheimer's disease where neuroinflammation has been associated with disease pathogenesis (Heneka et al., 2015. Lancet Neurol. 14(4):388-405).

Example 9: DMT, DET, DPT and 5-MeO-DMT prevent dopaminergic cell death and inflammation (Only Measured for DMT) caused by the potent and selective dopaminergic toxin 6-OHDA in an in vitro model of Parkinson's Disease. These desired effects are preserved in the presence of the 5-HT2A antagonist Ritanserin (Rit). Results from this example are shown in FIG. 9. The Human SH-SY5Y dopaminergic cell line was obtained from Sigma-Aldrich, cultured in 96-well plates and propagated in RPMI medium containing glutamine (1%) and 15% of fetal bovine serum (FBS) plus antibiotic (gentamicin), under humidified 5% $CO_2$ and 95% air. On attaining semiconfluence, separate groups of cells were treated with either: a) one of the four hallucinogenic tryptamines at 1 µM for 1 h, followed by 6-OHDA at 30 µM for 24 hours; or b) Rit at 1 µM for 1h, followed one of the four hallucinogenic tryptamines at 1 µM for an additional hour, at which point 6-OHDA was administered, also at 30 µM, and kept for 24 hours. Vehicle-treated cultures were used as controls. Cell cultures were then processed to assess cell viability (for all four tryptamines) and quantification of nitrite concentration (only performed in the DMT and DMT+Rit tests). Cell viability was measured using the MTT assay (Roche Diagnostic, GmbH), which is based on the ability of viable cells to reduce yellow MTT to blue formazan. After the aforementioned 24 h period in the presence of the different tryptamines or the respective tryptamine+Rit combinations, cells were incubated with MTT (0.5 mg/ml, 4 h) and subsequently solubilized in 10% SDS/0.01 M HCl for 12 h in the dark. The extent of MTT reduction was quantified by absorbance measurement at the 595 nm wavelength, as indicated in the instructions provided by the manufacturer. Nitrite quantification: Due to access to equipment problems at the time the experiments with DET, DPT and 5-MeO-DMT were conducted, the assessment of nitrite levels in the medium could only be done for the DMT experiments. These determinations were carried out as described in Example 8. Results from the cell viability tests are expressed as the percentage of viable dopaminergic cells measured. Results from nitrite determinations are expressed as actual concentrations (µM). Results from both techniques are presented in bar graphs. Each individual bar shows results as the mean±SEM of 6 replications in 3 different experiments.

FIG. 9 shows massive decreases in the percentage of viable dopaminergic cells, i.e. increased cell death, after administration of 6-OHDA alone, as compare to vehicle treated cells. Pre-treatment with each of the four hallucinogenic tryptamines tested, i.e., DMT, DPT, 5-MeO-DMT, and DET consistently and massively reduced cell death caused by the selective dopaminergic toxin 6-OHDA. This was evidenced by the significant increases in the percentage of viable dopaminergic neurons measured. As depicted in the upper panel of the figure where data from the DMT experiments is shown, 6-OHDA alone produced a marked increase in nitrite levels, indicating an active inflammatory process, analogous to that caused by LPS in glial cell cultures, as shown in Example 8. DMT pre-treatment significantly reduced the increased nitrite production brought about by 6-OHDA. The reduction in dopaminergic cell death produced the four tryptamines assessed was maintained for all of them in the presence of the selective 5-HT2A receptor antagonist Ritanserin. Additionally, the reduction of nitrite levels produced by DMT, was also preserved in the presence of Ritanserin.

Example 9 demonstrates: a) The novel unexpected finding that the DMT, DET, DPT and 5-MeO-DMT prevent dopaminergic cell death, and the associated inflammatory process (the latter assessment only conducted for DMT) in an in vitro model of Parkinson's Disease that makes use of 6-OHDA, a potent neurotoxic agent that causes highly selective damage to dopaminergic neurons; b) The novel and unexpected finding that all four tryptamines tested prevented dopaminergic cell death at the same concentration at which they promote neurogenesis. The fact that these compounds combine neurogenic effects, antiinflammatory activity and the protection against dopaminergic cell death demonstrated in this example, is quite remarkable and therapeutically very desirable. In the case of DMT, its anti-inflammatory effects shown in LPS-treated glial cells, were expanded in this example to the inflammation associated with dopaminergic cell loss in our in vitro model of Parkinson's Disease. The combination of beneficial effects displayed by these compounds suggests a high therapeutic potential specifically against Parkinson's Disease and potentially against other neurodegenerative disorders. They could tackle these disorders through at least two different and useful mechanisms: 1) by promoting formation of new neurons from endogenous neurogenic niches and thus potentially enhance a replacement of dying neurons; and 2) by slowing down the rate of disease progression by reducing the intensity of neural death. In contrast to these advantages, currently available medications used for instance to treat Parkinson's Disease, only alleviate its manifestations but don't reduce, let alone stop, the rate of dopaminergic cell death. Neurons keep dying, so that certain common treatments that require a remnant of live cells to show any efficacy (e.g. levodopa-based therapies), can initially work quite well and provide the patient with a false sense victory over the illness. As dopaminergic neurons keep disappearing, these treatments lose efficacy and eventually become totally ineffective once the levels of viable neurons fall below a minimum threshold; and c) The innovative finding that the protection against dopaminergic cell death brought about by hallucinogenic tryptamines (and against inflammation, at least for DMT is preserved in the presence of a 5-HT2A antagonist. Since 5-HT2A antagonists block the side effects of hallucinogenic tryptamines in humans, the proposed drug combination would retain the desired neuroprotective effect on dopaminergic neurons, while eliminating the undesired hallucinogenic effects.

Example 10: DMT administration prevents dopaminergic cell death in a in vivo model of Parkinson's disease. Results from this example are shown in FIG. 10. Adult male C57BL/6 mice (8-12 weeks old) were used in this study. Animals were properly anaesthetized and placed in a stereotaxic apparatus (Kopf Instruments, CA). 6-OHDA (5 µg in 2.5 ml PBS) was injected into the right side of the Substantia nigra pars compacta (SNpc) (coordinates from Bregma: posterior −3.2 mm; lateral +2.0 mm; ventral: +4.7 mm, according to the atlas of Paxinos and Franklin, The Mouse Brain in Stereotaxic Coordinates. 4. San Diego: Academic Press; 2012). Control animals of the same age were injected with PBS. A third group received an injection with 6-OHDA (5 µg) combined with DMT (0.1 µg) in 2.5 ml PBS. Mice were then housed individually to recover and sacrificed 3 weeks later. At this point animals were anaesthetized and perfused transcardially with a 4% paraformaldehyde solution. The brains were removed, postfixed in the same solution at 4° C. overnight, cryoprotected in 20% sucrose, frozen, and 30 μm coronal sections were obtained in a cryostat. Free-floating sections were processed for double fluorescent immunohistochemistry. After several rinses in PBS, brain sections were incubated with the following primary antibodies: mouse monoclonal anti-tyrosine-hydroxylase (TH; Sigma), to label dopaminergic cells, linked to a secondary Alexa-Fluor-647 goat anti-mouse antibody, combined with either: a) a rabbit anti-glial fibrillary acidic protein (GFAP; Sigma) antibody for the detection of astroglial cells, linked to a secondary Alexa-Fluor-488 goat anti rabbit antibody; or b) a rabbit anti-ba1 antibody (Wako) for the detection of microglial cells, linked to a secondary Alexa-Fluor-488 goat anti-rabbit antibody. Fluorescent images were acquired using a Radiance 2100 confocal microscope (Bio-Rad, Hercules, Calif.). To compare fluorescence signals from different preparations, confocal microscope settings were fixed for all samples within the same analysis and adjusted to produce the optimum signal-to-noise ratio. Each treatment condition (vehicle, 6-OHDA alone, and 6-OHDA+DMT) involved three separate experiments. Each experiment was carried out on four different animals. Neuronal integrity and specifically dopaminergic cell death was assessed by counting the percentage of TH$^+$ cells in the SNpc following a stereological approach. Confocal images of serial coronal sections (30 μm) containing the entire SNpc (rostrocaudal extent) were acquired under a ×63 objective to avoid oversampling errors. Every sixth section was selected to count the number of TH-positive cells, determining the boundaries of the SNpc with reference to internal anatomic landmarks (Paxinos and Frankling, The Mouse Brain in Stereotaxic Coordinates. 4. San Diego: Academic Press; 2012). Images were analyzed using computer-assisted image analysis software (Soft Imaging System Corporation, Lakewood, Colo.). Results were expressed as the percentage of dopaminergic cell loss in the SNpc.

FIG. 10 shows results: a) visually, using representative images; and b) numerically, by means of a bar graph. The images from animals administered 6-OHDA alone clearly show a decrease in the number of dopaminergic neurons present in the SNpc, together with an increase in the number of activated astroglial and microglial cells. These three effects are virtually absent in the images taken from animals that were administered 6-OHDA together with DMT. The bar graph shows the average percentage of cell loss obtained for each of the two drug-treated groups of animals (one injected with 6-OHDA alone, and another injected with 6-OHDA plus DMT). As shown in the graph, animals that were administered 6-OHDA alone suffered on average a 60% loss of dopaminergic cells. On the other hand, those animals that were administered 6-OHDA together with DMT, showed a much lower average percentage of dopaminergic cell loss. Thus, the presence of DMT reduced in live animals the magnitude of the average cell death provoked by the selective dopaminergic toxin 6-OHDA from a high 60% to a low 10%. Subjected to statistical analysis, the comparison between the two treatments showed that percentage cell death was significantly lower for the 6-OHDA+DMT combination.

Example 10 demonstrates: a) The novel and unexpected finding that the hallucinogenic tryptamine DMT prevents dopaminergic cell death and the associated inflammatory response (the latter shown only in the images) in an in vivo model of Parkinson's Disease; b) The novel finding that our previous in vitro findings are corroborated and strengthened by the positive results obtained for DMT in vivo. The prevention of dopaminergic cell death in a live animal, a much more complex system than a cellular culture increase the plausibility of potential effectiveness in humans. Although still not tested yet, the similar behavior displayed by other hallucinogenic tryptamines in previous examples, especially in Example 9, suggest that in vivo protection of dopaminergic neurons against cell death may be extended to additional tryptamines.

The invention claimed is:

1. A pharmaceutical combination product consisting of active ingredients (i), (ii) and, optionally, a monoamine oxidase inhibitor:
   (i) a compound described by the following formula (I), or salt thereof:

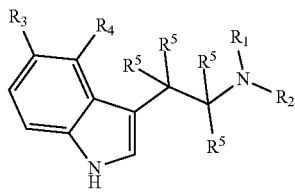

wherein,
   $R_1$ is selected from the group consisting of methyl, ethyl, n-propyl, allyl and isopropyl;
   $R_2$ is selected from the group consisting of methyl, ethyl, n-propyl, allyl and isopropyl;
   $R_3$ is selected from the group consisting of hydrogen, methoxy, methyl, hydroxy and a halogen; and
   $R_4$ is selected from the group consisting of hydrogen, hydroxy, phosphoryloxy and acetoxy;
   $R_5$ is selected from the group consisting of deuterium ($^2$H) and protium ($^1$H); and
   (ii) a 5-HT2A receptor antagonist.

2. The pharmaceutical combination product of claim 1, wherein the compound described by formula (I) is selected from the group consisting of N,N-dimethyltryptamine, 5-methoxy-N,N-dimethyltryptamine, N,N-diethyltryptamine, N,N-dipropyltryptamine, N,N-diisopropyltryptamine, 4-phosphoryloxy-N,N-dimethyltryptamine, 4-hydroxy-N,N-dimethyltryptamine and O-acetylpsilocin, or salt thereof.

3. The pharmaceutical combination product of claim 1, wherein the 5-HT2A receptor antagonist is selected from the group consisting of Methiothepin, Ritanserin, Ketanserin, Flibanserin, Methysergide, Trazodone, Nefazodone, Cinitapride, Cyproheptadine, Brexpiprazole, Cariprazine, Agomelatine, Pimavanserin, Eplivanserin, Volinanserin, Altanserin, Setoperone, LY-367,265, 1-(1-Naphthyl)piperazine, SB 206553, Pirenperone, SB-215505, Metergoline, Deramciclane, Amperozide, Glemanserin, 5-MeO-NBpBrT, Adatanserin, AMOA, Cinanserin, Fanansenrin, Iferanserin, AC-90179, LY86057, GSK-215083, Cyamemazine, Mesulergine, BF-1, LY215840, Sergolexole, Spiramide, LY53857, Amesergide, LY108742, Pipamperone, LY314228 and 5-I-R91150.

4. The pharmaceutical combination product of claim 1, wherein the combination product is prepared for oral, sublingual, buccal, intranasal, intravenous, intramuscular, subcutaneous, rectal, transdermal, topical and/or inhalation-mediated administration.

5. The pharmaceutical combination product of claim 1, wherein the compound described by formula (I), or salt thereof, and the 5-HT2A receptor antagonist are physically separated.

6. The pharmaceutical combination product of claim 1, wherein the 5-HT2A receptor antagonist alleviates or eliminates the hallucinogenic and/or psychedelic side effects caused by the compound described by formula (I).

7. The pharmaceutical combination product of claim 4, wherein the combination product prepared for oral, sublingual, or buccal administration is contained within one or two tablets, wherein the one or two tablets comprise a therapeutically effective amount of a compound described by formula (I), or salt thereof, and the 5-HT2A receptor antagonist for the treatment of a psychiatric or neurological disorder in a human.

8. The pharmaceutical combination product of claim 7, wherein the psychiatric disorder is selected from the group consisting of panic disorder, agoraphobia, social anxiety disorder, phobias, post-traumatic stress disorder, obsessive compulsive disorder, generalized anxiety disorder, bipolar disorder, depression, anorexia nervosa, binge eating disorder, bulimia nervosa, psychosis, schizophrenia, substance addiction and personality disorders.

9. The pharmaceutical combination product of claim 7, wherein the psychiatric disorder is depression, addiction, post-traumatic stress disorder, or a personality disorder.

10. The pharmaceutical combination product of claim 7, wherein the neurological disorder is Parkinson's Disease.

* * * * *